(12) United States Patent
Schoenberg et al.

(10) Patent No.: US 8,600,777 B2
(45) Date of Patent: Dec. 3, 2013

(54) MONITORING PATIENT CONDITIONS

(75) Inventors: Ido Schoenberg, Boston, MA (US); Eran David, Tel-Aviv (IL)

(73) Assignee: I.M.D. Soft Ltd., Tel Aviv (IL)

( * ) Notice: Subject to any disclaimer, the term of this patent is extended or adjusted under 35 U.S.C. 154(b) by 167 days.

(21) Appl. No.: 12/550,043

(22) Filed: Aug. 28, 2009

(65) Prior Publication Data

US 2010/0056875 A1    Mar. 4, 2010

Related U.S. Application Data

(60) Provisional application No. 61/092,527, filed on Aug. 28, 2008.

(51) Int. Cl.
*G06F 19/00* (2011.01)
(52) U.S. Cl.
USPC .............................................................. 705/3
(58) Field of Classification Search
USPC .................... 705/1, 2, 3; 600/300, 549, 508; 340/539.12
See application file for complete search history.

(56) References Cited

U.S. PATENT DOCUMENTS

| | | |
|---|---|---|
| 3,646,606 A | 2/1972 | Buxton et al. |
| 4,489,387 A | 12/1984 | Lamb et al. |
| 4,709,331 A | 11/1987 | Barkett et al. |
| 4,719,338 A | 1/1988 | Avery et al. |
| 4,731,725 A | 3/1988 | Suto et al. |
| 4,736,322 A | 4/1988 | Clifford |
| 4,807,170 A | 2/1989 | Kulli et al. |
| 4,835,372 A | 5/1989 | Gombrich et al. |
| 4,838,275 A | 6/1989 | Lee |
| 4,852,570 A | 8/1989 | Levine |
| 4,878,175 A | 10/1989 | Norden-Paul et al. |
| 5,065,315 A | 11/1991 | Garcia |
| 5,199,439 A | 4/1993 | Zimmerman et al. |
| 5,255,187 A | 10/1993 | Sorensen |
| 5,262,944 A | 11/1993 | Weisner et al. |
| 5,301,105 A | 4/1994 | Cummings, Jr. |
| 5,305,205 A | 4/1994 | Weber et al. |
| 5,307,263 A | 4/1994 | Brown |
| 5,321,800 A | 6/1994 | Lesser |
| 5,335,346 A | 8/1994 | Fabbio |

(Continued)

FOREIGN PATENT DOCUMENTS

| | | |
|---|---|---|
| EP | 0505627 | 9/1992 |
| WO | WO 98/29790 | 7/1998 |
| WO | WO 99/13766 | 3/1999 |
| WO | WO 00/79466 | 12/2000 |
| WO | WO 2005/067675 | 7/2005 |

OTHER PUBLICATIONS

International Search Report & Written Opinion in PCT application No. PCT/US10/25555, mailed Apr. 14, 2010, 7 pages.

(Continued)

*Primary Examiner* — John Pauls
(74) *Attorney, Agent, or Firm* — Fish & Richardson P.C.

(57) ABSTRACT

Among other things, a computer implemented method for monitoring patients released from an intensive care unit in a healthcare environment is described. The method comprises receiving medical information of a patient located at a location different from the intensive care unit, evaluating conditions of the patient by applying one or more rules to the medical information of the patient, and sending a message to the intensive care unit when the conditions of the patient match the one or more rules.

30 Claims, 6 Drawing Sheets

(56) References Cited

U.S. PATENT DOCUMENTS

| | | |
|---|---|---|
| 5,348,008 A | 9/1994 | Bornn et al. |
| 5,361,202 A | 11/1994 | Doue |
| 5,398,300 A | 3/1995 | Levey |
| 5,404,292 A | 4/1995 | Hendrickson |
| 5,417,717 A | 5/1995 | Salo et al. |
| 5,447,164 A | 9/1995 | Shaya et al. |
| 5,482,050 A | 1/1996 | Smokoff et al. |
| 5,544,649 A | 8/1996 | David et al. |
| 5,544,661 A | 8/1996 | Davis et al. |
| 5,572,422 A | 11/1996 | Nematbakhsh et al. |
| 5,574,828 A | 11/1996 | Hayward et al. |
| 5,576,952 A | 11/1996 | Stutman et al. |
| 5,592,945 A | 1/1997 | Fiedler |
| 5,594,638 A | 1/1997 | Iliff |
| 5,619,991 A | 4/1997 | Sloane |
| 5,630,664 A | 5/1997 | Farrelly |
| 5,640,953 A | 6/1997 | Bishop et al. |
| 5,678,562 A | 10/1997 | Sellers |
| 5,682,526 A | 10/1997 | Smokoff et al. |
| 5,687,717 A | 11/1997 | Halpern et al. |
| 5,701,894 A | 12/1997 | Cherry et al. |
| 5,704,350 A | 1/1998 | Williams, III |
| 5,713,350 A | 2/1998 | Yokota et al. |
| 5,715,451 A | 2/1998 | Marlin |
| 5,722,999 A | 3/1998 | Snell |
| 5,724,580 A | 3/1998 | Levin et al. |
| 5,729,479 A | 3/1998 | Golan |
| 5,752,621 A | 5/1998 | Passamante |
| 5,772,585 A | 6/1998 | Lavin et al. |
| 5,772,601 A | 6/1998 | Oka et al. |
| 5,781,442 A | 7/1998 | Engleson et al. |
| 5,794,208 A | 8/1998 | Goltra |
| 5,801,755 A | 9/1998 | Echerer |
| 5,822,544 A | 10/1998 | Chaco et al. |
| 5,823,948 A | 10/1998 | Ross, Jr. et al. |
| 5,830,150 A | 11/1998 | Palmer et al. |
| 5,832,450 A | 11/1998 | Myers et al. |
| 5,839,438 A | 11/1998 | Graettinger et al. |
| 5,842,173 A * | 11/1998 | Strum et al. ............... 705/2 |
| 5,842,976 A | 12/1998 | Williamson |
| 5,842,978 A | 12/1998 | Levy |
| 5,845,255 A | 12/1998 | Mayaud |
| 5,855,550 A | 1/1999 | Lai et al. |
| 5,860,918 A | 1/1999 | Schradi et al. |
| 5,867,821 A | 2/1999 | Ballantyne et al. |
| 5,868,669 A | 2/1999 | Iliff |
| 5,899,855 A | 5/1999 | Brown |
| 5,912,656 A | 6/1999 | Tham et al. |
| 5,921,920 A | 7/1999 | Marshall et al. |
| 5,924,074 A | 7/1999 | Evans |
| 5,940,815 A | 8/1999 | Maeda et al. |
| 5,942,986 A | 8/1999 | Shabot et al. |
| 5,956,689 A | 9/1999 | Everhart, III |
| 5,970,463 A | 10/1999 | Cave et al. |
| 5,987,519 A | 11/1999 | Peifer et al. |
| 5,997,476 A | 12/1999 | Brown |
| 6,024,699 A | 2/2000 | Surwit et al. |
| 6,047,259 A | 4/2000 | Campbell et al. |
| 6,061,657 A | 5/2000 | Whiting-O'Keefe |
| 6,093,146 A | 7/2000 | Filangeri |
| 6,101,478 A | 8/2000 | Brown |
| 6,102,856 A | 8/2000 | Groff et al. |
| 6,112,182 A | 8/2000 | Akers et al. |
| 6,154,668 A | 11/2000 | Pedersen et al. |
| 6,168,563 B1 | 1/2001 | Brown |
| 6,206,829 B1 | 3/2001 | Iliff |
| 6,215,403 B1 | 4/2001 | Chan et al. |
| 6,225,901 B1 | 5/2001 | Kail, IV |
| 6,230,142 B1 | 5/2001 | Benigno et al. |
| 6,233,581 B1 | 5/2001 | Rambaud et al. |
| 6,234,964 B1 | 5/2001 | Iliff |
| 6,238,338 B1 | 5/2001 | DeLuca et al. |
| 6,245,013 B1 | 6/2001 | Minoz et al. |
| 6,254,536 B1 | 7/2001 | Devito |
| 6,278,999 B1 | 8/2001 | Knapp |
| 6,283,761 B1 | 9/2001 | Joao |
| 6,292,698 B1 | 9/2001 | Duffin et al. |
| 6,304,788 B1 | 10/2001 | Eady et al. |
| 6,315,719 B1 | 11/2001 | Rode et al. |
| 6,322,502 B1 | 11/2001 | Schoenberg et al. |
| 6,363,393 B1 | 3/2002 | Ribitzky |
| 6,364,834 B1 * | 4/2002 | Reuss et al. ............... 600/300 |
| 6,381,576 B1 | 4/2002 | Gilbert |
| 6,385,589 B1 | 5/2002 | Trusheim et al. |
| 6,398,728 B1 | 6/2002 | Bardy |
| 6,413,224 B1 | 7/2002 | Ogura et al. |
| 6,442,433 B1 | 8/2002 | Linberg |
| 6,463,320 B1 | 10/2002 | Xue et al. |
| 6,658,276 B2 | 12/2003 | Kianl et al. |
| 6,700,028 B2 | 3/2004 | Dyroff |
| 6,748,353 B1 | 6/2004 | Iliff |
| 6,768,999 B2 | 7/2004 | Prager et al. |
| 6,804,558 B2 | 10/2004 | Haller et al. |
| 6,804,656 B1 | 10/2004 | Rosenfeld et al. |
| 6,893,396 B2 | 5/2005 | Schulze et al. |
| 6,941,271 B1 | 9/2005 | Soong |
| 7,039,878 B2 | 5/2006 | Auer et al. |
| 7,374,535 B2 | 5/2008 | Schoenberg et al. |
| 7,778,851 B2 | 8/2010 | Schoenberg et al. |
| 7,831,450 B2 | 11/2010 | Schoenberg et al. |
| 7,848,935 B2 | 12/2010 | Gotlib et al. |
| 7,899,683 B2 | 3/2011 | Schoenberg et al. |
| 8,027,846 B2 | 9/2011 | Schoenberg et al. |
| 2001/0044588 A1 * | 11/2001 | Mault ............... 600/549 |
| 2002/0038392 A1 | 3/2002 | De La Huerga |
| 2002/0087355 A1 | 7/2002 | Rowlandson |
| 2002/0099273 A1 | 7/2002 | Bocionek et al. |
| 2002/0173988 A1 | 11/2002 | Dang |
| 2002/0177758 A1 | 11/2002 | Schoenberg et al. |
| 2002/0177759 A1 | 11/2002 | Schoenberg et al. |
| 2002/0187483 A1 | 12/2002 | Hoffman et al. |
| 2003/0036687 A1 | 2/2003 | Schoenberg et al. |
| 2003/0163351 A1 | 8/2003 | Brown et al. |
| 2004/0034550 A1 | 2/2004 | Menschik et al. |
| 2004/0082845 A1 | 4/2004 | Matsumoto et al. |
| 2004/0111296 A1 | 6/2004 | Rosenfeld |
| 2004/0111297 A1 | 6/2004 | Schoenberg |
| 2004/0111298 A1 | 6/2004 | Schoenberg |
| 2004/0111622 A1 | 6/2004 | Schoenberg |
| 2004/0152952 A1 | 8/2004 | Gotlib et al. |
| 2004/0153343 A1 | 8/2004 | Gotlib et al. |
| 2004/0172300 A1 | 9/2004 | Mihai et al. |
| 2004/0225629 A1 | 11/2004 | Eder |
| 2005/0055244 A1 | 3/2005 | Mullan et al. |
| 2005/0086071 A1 | 4/2005 | Fox, Jr. et al. |
| 2005/0108057 A1 | 5/2005 | Cohen et al. |
| 2005/0125256 A1 | 6/2005 | Schoenberg et al. |
| 2005/0144043 A1 | 6/2005 | Holland et al. |
| 2005/0159987 A1 | 7/2005 | Rosenfeld et al. |
| 2005/0206518 A1 * | 9/2005 | Welch et al. ............ 340/539.12 |
| 2005/0222873 A1 | 10/2005 | Nephin et al. |
| 2005/0234739 A1 | 10/2005 | Schoenberg |
| 2005/0256815 A1 | 11/2005 | Reeve et al. |
| 2006/0004610 A1 | 1/2006 | David |
| 2007/0083111 A1 | 4/2007 | Hossack et al. |
| 2007/0125844 A1 | 6/2007 | Libin et al. |
| 2007/0162308 A1 | 7/2007 | Peters |
| 2008/0149701 A1 | 6/2008 | Lane |
| 2008/0208618 A1 | 8/2008 | Schoenberg et al. |
| 2008/0228090 A1 * | 9/2008 | Wariar et al. ............... 600/508 |
| 2008/0257961 A1 | 10/2008 | Lubow |
| 2008/0306770 A1 * | 12/2008 | Sysko et al. ............... 705/3 |
| 2009/0043611 A1 | 2/2009 | Nadas et al. |
| 2010/0056875 A1 | 3/2010 | Schoenberg et al. |
| 2010/0217621 A1 | 8/2010 | Schoenberg et al. |
| 2010/0217623 A1 | 8/2010 | Schoenberg et al. |
| 2010/0268552 A1 | 10/2010 | Schoenberg et al. |

OTHER PUBLICATIONS

Andrews, Robert D. et al., "Computer Charting: An Evaluation of a Respiratory Care Computer System" *Respiratory Care*, vol. 30, No. 8, Aug. 1985; pp. 695-707.

(56) References Cited

OTHER PUBLICATIONS

Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Avila, Lorene S. and M. Michael Shabot, "Keys to the Successful Implementation of an ICU Patient Data Management System," *International Journal of Clinical Monitoring and Computing*, vol. 5, 1988, pp. 15-25.

Ayres, Stephen M. et al. Textbook of Critical Care, 3rd Edition, 1995, Harcourt Brace & Company. Sections IV & V.

Bates, David W. et al., "Reducing the Frequency of Errors in Medicine Using Information Technology" *Journal of the American Medical Informatics Association*, vol. 8, No. 4, Jul./Aug. 2001; pp. 299-308.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Berg, et al. "Remote Critical Care Consultation: Telehealth projection of clinical specialty expertise". Tripler Army Medical Center, Honolulu.

Bierman, M. I. et al., "Pulse Oximetry in the Postoperative Care of Cardiac Surgical Patients; A Randomized Controlled Trial." *Chest*, vol. 102, No. 5, Nov. 1992: 1367-1370.

Borzo, Greg, "Web Technology, Coming to a Hospital Near You," amednews.com, The Newspaper for America's Physicians, Nov. 18, 1996, Retrieved from Internet, pp. 1-4.

Bradshaw, Karen E. et al., "Development of a Computerized Laboratory Alerting System" *Computers and Biomedical Research*, vol. 22, 1989; pp. 575-587.

Bradshaw, K. E., "Computerized Alerting System Warns of Life-Threatening Events." In Symposium on Computer Application in Medical Care, Oct. 25-26, 1986, Washington, DC; pp. 403-409.

Bradshaw, Karen E. et al., "Computer-Based Data Entry for Nurses in the ICU." *M. D. Computing*, vol. 6, No. 5, 1989; pp. 274-280.

Bradshaw, Karen E. et al., "Improving Efficiency and Quality in a Computerized ICU" 1988 SCAMC, Inc., pp. 763-767.

Bradshaw, Karen E. et al., "Physician Decision Making—Evaluation of Data used in a Computerized ICU" *International Journal of Clinical Monitoring and Computing*, vol. 1, 1984; pp. 81-91.

Cannon, Scott R. and Reed M. Gardner, "Experience with a Computerized Interactive Protocol System Using HELP" *Computers and Biomedical Research*, vol. 13, 1980; pp. 399-409.

Capuano, Terry Ann et al. Remote Telemetry, Nursing Management, Vo.26, No. 7, Jul. 1995, p. 26.

Chizeck, H. J., "Modelling, Simulation and Control in a Data Rich Environment." In Symposium on Computer Applications in Medical Care, Oct. 25-26, 1986, Washington, DC; pp. 65-69.

Chu, Wesley W. et al. "A Medical Digital Library to Support Scenario and User-Tailored Information Retrieval." *Transactions on Information Technology in Biomedicine*, vol. 4, No. 2, Jun. 2000, pp. 97-107.

Clayton, P. D. et al., "Bringing HELP to the Clinical Laboratory—Use of an Expert System to Provide Automatic Interpretation of Laboratory Data" *Ann Clin Biochem*, vol. 24, Supplement, 1987; pp. S1-5 to S1-11.

Clayton, P.D. et al., "Data Driven Interpretation of Laboratory Results in the Context of a Medical Decision Support System" *Clinical Biochemistry, Principles-Methods, Applications 2*, Data Presentation Interpretation (Eds. H. Keller and Ch. Trendelenburg), Walter deGruyter, Berlin—New York, 1989; Chapter 3.7; pp. 367-380.

Clemmer, T. P. et al, "Computer Support in Critical Care Medicine" Proceedings of the Fourth Annual Symposium on Computer Applications in Medical Care, Part III, Nov. 2-5, 1980, Washington, D.C.; pp. 1557-1561.

Clemmer, Terry P. and Reed M. Gardner, "Data Gathering, Analysis, and Display in Critical Care Medicine" *Respiratory Care*, vol. 30, No. 7, Jul. 1985; pp. 586-601.

Clemmer, Terry P. and Reed M. Gardner, "Medical Informatics in the Intensive Care Unit: State of the Art 1991" *International Journal of Clinical Monitoring and Computing*, vol. 8, 1992; pp. 237-250.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgy, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

DeLima, Marie et al., "Successful Implementation of a Multiple-ICU Clinical Information System in a Tertiary Care Medical Center" AMIA 2000 Annual Symposium; Session S62—Poster Session 2.

de Oliveira, Guedes P. et al., "The Role of Computer Based Techniques in Patient Monitoring: Technical Note." *Acta Neuorchir*, vol. 55, 1992 (Suppl.): 18-20.

Doctors use 'remote control' to monitor ICU patients, CNN.com. technology>computing, Aug. 21, 2000, http://www.cnn.com/2000/TECH/computing/08/21/icu..t_t/.

Duncan, Ray and Jeffrey J. Pomerance, "Computer Assistance in Delivery of Patient Care in a Neonatal Intensive Care Unit," *The Use of Computers in Perinatal Medicine*, Chapter 19, Abstract only, 1982, Retrieved online from: Neonatology on the Web.

Duncan, Ray, "Computer Assisted Care in the Neonatal Intensive Care Unit," *The Use of Computers in Perinatal Medicine*, Proceedings of the 17th Annual Symposium on Computer Applications in Medical Care, American Medical Informatics Association, Abstract only, Nov. 1993, Retrieved online from: Neonatology on the Web.

East, T. D. et al., "A Strategy for Development of Computerized Critical Care Decision Support Systems," *Int J Clin Monit Comput*, vol. 8, No. 4, Abstract only, 1991-1992, Retrieved online from: PubMed.

East, Thomas D. et al., "Computers in Critical Care" *Critical Care Nursing Clinics of North America*, vol. 7, No. 2, Jun. 1995; pp. 203-216.

East, Thomas D. et al., "Development of Computerized Critical Care Protocols—A Strategy That Really Works!" Proceedings of 14th Symposium on Computer Applications in Medical Care, 1990; pp. 564-568.

East, Thomas D. et al., "Digital Electronic Communication between ICU Ventilators and Computers and Printers" *Respiratory Care*, vol. 37, No. 9, Sep. 1992; pp. 1113-1123.

East, Thomas D. et al., "Implementation Issues and Challenges for Computerized Clinical Protocols for Management of Mechanical Ventilation in ARDS Patients" SCAMC 1989: 13: 583-587.

Elliott, C. Gregory et al., "Computer-assisted Medical Direction of Respiratory Care" *Respiratory Management*, vol. 19, No. 2, 1989; pp. 31-35.

Evans, R. Scott et al., "A Computerized Approach to Monitor Prophylactic Antibiotics" 1987 SCAMC, Inc., 241-245.

Evans, R. Scott et al., "Computer Surveillance of Hospital-Acquired Infections and Antibiotic Use" *JAMA*, vol. 256, No. 8, Aug. 22/29, 1986; pp. 1007-1011.

Evans, R. Scott et al., "Development of a Computerized Adverse Drug Event Monitor" Proc Annu Symp Comput Appl Med Care. 1991; pp. 23-27.

Evans, R. Scott et al., "Development of a Computerized Infectious Disease Monitor (CIDM)" *Computers and Biomedical Research*, vol. 18, 1985; pp. 103-113.

Evans, R. Scott et al., "Prediction of Hospital Infections and Selection of Antibiotics Using and Automated Hospital Database." 1990 SCAMC, Inc.; pp. 663-667.

Evans, R. Scott et al., "Reducing the Duration of Prophylactic Antibiotic Use Through Computer Monitoring of Surgical Patients" *DICP, The Annals of Pharmacotherapy*, vol. 24, Apr. 1990; pp. 351-354.

Factor, Michael et al., "Real-Time Data Fusion in the Intensive Care Unit," *IEEE. Computer*, Abstract only, Nov. 1991, Retrieved online from: Neonatology on the Web.

Fischer, Joachim E. et al., "Quantifying Uncertainty: Physicians' Estimates of Infection in Critically Ill Neonates and Children" *CID*, vol. 38, May 15, 2004; pp. 1383-1390.

(56) References Cited

OTHER PUBLICATIONS

Fitzpatrick, Geraldine, "TARDIS Evaluation, Report on Final Usage Evaluation of the TARDIS Telehealth System" Distributed Systems Technology Centre, DSTC Pty. Ltd., Jul. 24, 1998; pp. 1-54.

Fleegler et al. "Apache III, Equation Update—version III-I ("eye")" (Note: Includes Validation of Mortality Equations Carried Over to Version III-J)" White Paper Report, Aug. 1998, Cerner Corporation; pp. 1-13.

Fleegler et al. "Apache III, Equation Update (Version III-J)" White Paper Report, Oct. 2002, Cerner Corporation; pp. 1-22.

Frize, Monique and Robin Walker, "Clinical Decision-Support Systems for Intensive Care Units Using Case-Based Reasoning" *Med Eng Phys*, vol. 22, No. 9, 2000; pp. 671-677.

Fumai, N. et al., "Database Design of an Intensive Care Unit Patient Data Management System," *Proceedings of the Fourth Annual IEEE Symposium on Computer-Based Medical Systems*, Abstract only, IEEE Computer Society Press, Los Alamitos, CA, May 12, 1991, Retrieved online from: Neonatology on the Web.

Furst, Emmanuel, "Cardiovascular Technology" *J Cardiovasc Nurs*, vol. 4, No. 1, 1989; pp. 68-78.

Galfalvy, H.C. et al., "Evaluation of Community Care Network (CCN) System in a Rural Health Care Setting" 1995 AMIA, Inc.; pp. 698-702.

Gardner, R.M, "Computers in the ICU and Surgery-Keeping Real-Time Patient Records for Decision-Making." pp. 151-157.

Gardner, Reed M, "Computerized Management of Intensive Care Patients," *M.D. Computing*, vol. 3, No. 1, Abstract only, 1986, Retrieved online from: Neonatology on the Web.

Gardner, Reed M. "Integrated Computerized Records Provide Improved Quality of Care with Little Loss of Privacy" *Journal of the American Medical Informatics Association*, vol. 1, No. 4, Jul./Aug. 1994; pp. 320-322.

Gardner, Reed M. and Karen W. Hollingsworth, "ECG and Pressure Monitoring: How to Obtain Optimal Results" The Society of Critical Care Medicine: Textbook of Critical Care, Second Edition, W.B. Saunders, Co.: Philadelphia, PA, USA, 1989; Chapter 33; pp. 295-305.

Gardner, Reed M. and M. Michael Shabot, "Computerized ICU Data Management: Pitfalls and Promises" *International Journal of Clinical Monitoring and Computing*, vol. 7, 1990; pp. 99-105.

Gardner, Reed M. and M. Michael Shabot, "Computerized ICU Data Management: Pitfalls and Promises," *International Journal of Clinical Monitoring and Computing*, vol. 7, Abstract only, 1990, Retrieved online from: Neonatology on the Web.

Gardner, Reed M. and R. Scott Evans, "Computer-Assisted Quality Assurance" *Group Practical Journal*, vol. 41, No. 3., May/Jun. 1992; pp. 8-11.

Gardner, Reed M. and Terry P. Clemmer, "Computerized Protocols Applied to Acute Patient Care" *Advances in Automated Analysis*, vol. 1, Technicon International Congress 1976, Mediad Incorporated, Tarrytown, NY; pp. 158-193.

Gardner, Reed M. and William L. Hawley, "Standardizing Communications and Networks in the ICU" Patient Monitoring and Data Management, Managing Patient Data, 1985 AAMI; pp. 59-63.

Gardner, Reed M. et al, "Integrated Computer Systems for Monitoring of the Critically Ill" Proc. Comput. Appl. Med. Care, 1977, pp. 301-307.

Gardner, Reed M. et al., "Assessing the Effectiveness of a Computerized Pharmacy System" Proceedings of the Fourteenth Annual Symposium on Computer Applications in Medical Care, Washington, DC, Nov. 4-7, 1990; pp. 668-672.

Gardner, Reed M. et al., "Computer-based ICU Data Acquisition as an Aid to Clinical Decision-Making" *Critical Care Medicine*, vol. 10, No. 12, Dec. 1982; pp. 823-830.

Gardner, Reed M. et al., "Computer-Critiqued Blood Ordering Using the HELP System" *Computers and Biomedical Research*, vol. 23, 1990; pp. 514-528.

Gardner, Reed M. et al., "Computerized Blood Gas Interpretation and Reporting System" *Computer Magazine*, Jan. 1975; pp. 39-45.

Gardner, Reed M. et al., "Computerized Medical Care: The HELP System at LDS Hospital" *Journal of AHIMA*, vol. 63, No. 6, 1992; pp. 68-78.

Gardner, Reed M. et al., "Computers in the Emergency Room" *Internal Medicine for the Specialist*, vol. 8, No. 3, Mar. 1987; pp. 105-114.

Gardner, Reed M. et al., "Computers in the Intensive Care Unit: A Match Meant to Be!" *Textbook of Critical Care*, Chapter 196, Third Edition, W.B. Saunders Company, 1995; pp. 1757-1770.

Gardner, Reed M. et al., "Computers in the Intensive Care Unit: Match or Mismatch?" The Society of Critical Care Medicine: Textbook of Critical Care, Second Edition, W.B. Saunders, Co.: Philadelphia, PA, USA, 1989; Chapter 26: pp. 248-259.

Gardner, Reed M. et al., "Distributed Data Base and Network for ICU Monitoring" IEEE Computers in Cardiology, Salt Lake City, Utah, Sep. 18-24, 1984; pp. 305-307.

Gardner, Reed M. et al., "Eight-Channel Data Set for Clinical EEG Transmission Over Dial-Up Telephone Network" IEEE Transactions on Biomedical Engineering, vol. BME-21, No. 3, May 1974; pp. 246-249.

Gardner, Reed M. et al., "Integrated Computer Network for Acute Patient Care" Proceedings of 1984 Symposium on Computer Applications in Medical Care, Nov. 4-7, 1984, Washington, D.C.; pp. 185-188.

Gardner, Reed M. et al., "Monitoring Direct Blood Pressure: Algorithm Enhancements" IEEE Comput Cardiol 1986;13:607-610.

Gardner, Reed M. et al., "Real Time Data Acquisition: Experience With the Medical Information Bus (MIB)" Proc Annu Symp Comput Appl Med Care. 1991; pp. 813-817.

Gardner, Reed M. et al., "The HELP Hospital Information System: Update 1998," *International Journal of Medical Informatics*, vol. 54, pp. 169-182, 1999.

Gardner, Reed M., "Computerized Alert System Use in Clinical Medicine" 1979 IEEE, pp. 136-140.

Gardner, Reed M., "Computerized Data Management and Decision Making in Critical Care" Symposium on Critical Care, *Surgical Clinics of North America*, vol. 65, No. 4, Aug. 1985; pp. 1041-1051.

Gardner, Reed M., "Computerized Intensive Care Monitoring at LDS Hospital—Progress and Development" IEEE-NIH Conference on Computers in Cardiology, Oct. 1974; pp. 97-105.

Gardner, Reed M., "Computerized Management of Intensive Care Patients" *Images, Signals and Devices*, vol. 3, No. 1, 1986; pp. 36-51.

Gardner, Reed M., "Computerized Patient Monitoring at LDS Hospital—An Evaluation" Proceedings of the San Diego Biomedical Symposium, 1971; vol. 10; pp. 151-159.

Gardner, Reed M., "Computers in Critical Care" *Wellcome Trends in Hospital Pharmacy*, Jul. 1992; p. 6-8.

Gardner, Reed M., "Computers in the ICU" *Medical Electronics*, Jun. 1984; pp. 129-135.

Gardner, Reed M., "Information Management—Hemodynamic Monitoring" *Seminars in Anesthesia*, vol. II, No. 4, Dec. 1983; pp. 287-299.

Gardner, Reed M., "Monitoring of Physiological Data in a Clinical Environment" Annual Review of Biophysics and Bioengineering, vol. 1, 1972; pp. 211-224.

Gardner, Reed M., "Patient-Monitoring Systems" Medical informatics: computer applications in health care table of contents, Chapter 12, pp. 366-399. Wesley Longman Publishing Co., Inc. Boston, MA, USA, 1990.

Gardner, Reed M., "Tomorrow's Electronic Hospital is Here Today" *IEEE Spectrum*, Jun. 1984; pp. 101-103.

Gardner, Reed M. "Performance of Computerized Protocols for the Management of Arterial Oxygenation in an Intensive Care Unit," International Journal of Clinical Monitoring and Computing 8, 1992, 271-180, Kluwer Academic Publishers, Netherlands.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

(56) References Cited

OTHER PUBLICATIONS

Gray, J.E. et al., "Baby CareLink: Using the Internet and Telemedicine to Improve Care for High-risk Infants," *Pediatrics*, vol. 106, No. 6, Abstract only, Dec. 2000, Retrieved online from: Neonatology on the Web.

Grundy, Betty L. et al., "Telemedicine in Critical Care: An Experiment in Health Care Delivery" *JACEP*, vol. 6, No. 10., Oct. 1977; pp. 439-444.

Grundy, Betty Lou et al., "Telemedicine in Critical Care: Problems in Design, Implementation, and Assessment" *Critical Care Medicine*, vol. 10, No. 7, Jul. 1982; pp. 471-475.

Hahnel, J. et al., "Can a Clinician Predict the Technical Equipment a Patient will Need During Intensive Care Unit Treatment? An Approach to Standardize and Redesign the Intensive Care Unit Workstation." *J. Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Halpern, Neil A. et al., "Critical Care Medicine in the United States 1985-2000: An Analysis of Bed Numbers, Use, and Costs" *Crit Care Med*, vol. 32, No. 6, 2004; pp. 1254-1259.

Haug, Peter J. et al., "Decision Support in Medicine: Examples from the HELP System" *Computers and Biomedical Research*, vol. 27, 1994: pp. 396-418.

Haug, Peter J. et al., "Hospital-Based Decision Support," *Clinical Decision Support Systems, Theory and Practice*, Springer-Verlag New York Inc., 1994; pp. 77-103.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Henderson, Susan E. et al., "Computerized Clinical Protocols in an Intensive Care Unit: How Well Are They Followed?" 1990 SCAMC, Inc.; 284-288.

Henderson, Susan et al., "Performance Evaluation of Computerized Clinical Protocols for Management of Arterial Hypoxemia in ARDS Patients" Proc. 13th Annual Symp. Comput. Appl. Med. Care. 1989. Washington, D.C., pp. 588-592.

Henderson, Susan et al., "Performance of Computerized Protocols for the Management of Arterial Oxygenation in an Intensive Care Unit" *International Journal of Clinical Monitoring and Computing*, vol. 8, 1992; pp. 271-280.

Henkind, S.J., et al., "A Clinical Alarm System Using Techniques from Artificial Intelligence and Fuzzy Set Theory," *Approximate Reasoning in Intelligent Systems, Decision and Control*, Pergamon Press, 1987, pp. 91-104.

Henkind, Steven et al. "Intensive Care Unit Monitoring Using a Real-Time Expert System," *Computers in Cardiology*, Sep. 18-21, Salt Lake City, Utah, 1994, pp. 7-12.

Heterington. "High tech meets high touch: telemedicine's contribution to patient wellness". Nursing Administration Quarterly, 22(3), Spring 1998.

Hosseinzadeh, Abolfazl, "A Rule-Based System for Vital Sign Monitoring in Intensive Care", Department of Electrical Engineering, McGill University, Montreal; Nov. 1993.

Hripcsak, George et al., "Design of a Clinical Event Monitor," *Computers and Biomedical Research*, vol. 29, No. 3, Abstract only, Jun. 1996, Retrieved online from: Neonatology on the Web.

Hulse, Russell K. et al., "Computerized Medication Monitoring System" *American Journal of Hospital Pharmacy*, vol. 33, Oct. 1976; pp. 1061-1064.

Ingenerf, Josef. "Telemedicine and Terminology: Different Needs of Context Information." *Transactions on Information Technology in Biomedicine*, vol. 3, No. 2, Jun. 1999, pp. 92-100.

Irazurta, Jose, "Monitoring in Pediatric Intensive Care." *Indian J. Pediatrics*, vol. 60, 1993: 55-65.

Jamzad et al. "A human friendly reporting and database system for brain PET analysis" Annals of Nuclear Medicine 10(1):99-104, 1996.

Janofsky, Michael, "Finding Value in Intensive Care, from Afar," The New York Times on the Web, Jul. 27, 1999, www.Visicu.com/companynews/0799_nytimes.htm.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems." *Critical Care Medicine*, vol. 23, No. 10, Oct. 1995: 1745-1755.

Johnson, Bob et al., *Discern—An Integrated Prospective Decision Support System*, Symposium on Computer Applications in Medical Care. A Conference of the American Medical Informatics Associated, Nov. 5-19, 1994, Washington, D.C. p. 969.

Johnson, Dickey Seidlitz et al., "A Computerized Alert Program for Acutely Ill Patients" *Journal of Nursing Administration*, Jun. 1980; pp. 26-35.

*Jury Verdict in Cerner Corporation v. Visicu, Inc.*, Civil Action No. 04-1033 (W.D. Mo., Judge Gary A. Fenner), filed Dec. 8, 2009, 5 pages.

Kaplan, Simon M. et al. Designing Support for Remote Intensive-Care Telehealth Using the Locales Framework, ACM, 1997, 99.173-184.

Kassirer, Jerome P., "The Next Transformation in the Delivery of Health Care (Editorial)," *NEJM*, vol. 332, No. 1, Abstract only, Jan. 5, 1995, Retrieved online from: Neonatology on the Web.

Keller, H. et al. Data Presentation Interpretation, Clinical Biochemistry Principles, Methods, Applications, Walter-deGruyter & Co., 1989.

Kimura, Michio et al. "MERIT-9: a patient information exchange guideline using MML, HL7, and DICOM." International Journal of Medical Informatics, vol. 51, No. 1, Jul. 1998, pp. 59-68.

Klaas, M. A. & E. Y. Cheng, "Early Response to Pulse Oximetry Alarms with Telemetry." *J. Clinical Monitoring*, vol. 10, No. 3, May 1994: 178-180.

Kleinholz, Lutz et al. "Supporting Cooperative Medicine: The Bermed Project." *IEEE Multimedia*, vol. 1, No. 4, Dec. 1994, pp. 44-53.

Kohane, I. S. et al., "Hypothesis-Driven Data Abstraction with Trend Templates." In Symposium on Computer Applications in Medical Care, Oct. 30-Nov. 3, 1993, Washington, DC; pp. 444-448.

Kontaxis, K.M. et al. "Using XML and Controlled Vocabularies to Achieve Unambiguous Knowledge Acquistion From Multiple Hetereogeneous Medical Data Sources." *Information Technology Applications in Biomedicine*, 4th International IEEE EMBS Special Topic Conference on Apr. 24-26, 2003, pp. 161-164.

Koski, E. M. J. et al., "A Knowledge-Based Alarm System for Monitoring Cardiac Operated Patients—Assessment of Clinical Performance." *International J Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Kostopoulou, O. and M. Wildman, "Sources of Variability in Uncertain Medical Decisions in the ICU: a Process Tracing Study" *Qual Saf Health Care*, vol. 13, 2004; pp. 272-280.

Kuperman, Gil et al., "Continuous Quality Improvement Applied to Medical Care: Experiences at LDS Hospital" *Medical Decision Making*, vol. 11, No. 4, Oct.-Dec. 1991 Supplement; pp. S60- S65.

Kuperman, Gilad J. & Reed M. Gardner, "The Help System. A Snapshot in Time." Department of Biophysics, LDS Hospital, Salt Lake City, Utah, Sep. 1988; pp. 1-295.

Kuperman, Gilad J. et al., "Clinical Decision Support for Hospital and Critical Care" *Journal of Healthcare Information Management*, vol. 13, No. 2, Summer 1999; pp. 81-96.

Kuperman, Gilad J., Reed M. Gardner and T. Allan Pryor, "HELP: A Dynamic Hospital Information System," *Computers and Medicine*, Springer-Verlag New York Inc., 1991; 174 pages (unnumbered).

L'Estrange, P. R. et al., "A Microcomputer System for Physiological Data Collection and Analysis." *Australian Dental Journal*, vol. 38, No. 5, Oct. 1993: 400-405.

(56) References Cited

OTHER PUBLICATIONS

Laffel, G. et al., "Using Control Charts to Analyze Serial Patient-Related Data." *Quality Management in Health Care*, vol. 3, No. 1, Fall 1994: 70-77.
Larsen, Robert A. et al., "Improved Perioperative Antibiotic Use and Reduced Surgical Wound Infections Through Use of Computer Decision Analysis." *Infect Control Hosp Epidemiol*, vol. 10, No. 7, 1989; pp. 316-320.
Laurenson, R.C., "Computer Software 'Article of Manufacture' Patents," *JPTOS*,:811-824 (1995) Previously appeared in *Computer Law Reporter*, 21(6):965-974 (1995).
Lee, Ho Sung et al., "Remote Patient Monitoring Service through World-Wide Web" Proceedings—19$^{th}$ International Conference—IEEE/EMBS Oct. 30- Nov. 2, Chicago, IL. USA; pp. 928-931.
Lepage, E. et al., "Development of a Computerized Knowledge Based System Integrated to a Medical Workstation: Application to Blood Transfusion" IMIA 1992; pp. 585-590.
Lepage, Eric F. et al., "Assessing the Effectiveness of a Computerized Blood Order "Consultation" System" 1992 AMIA, Inc.; pp. 33-37.
Lewis, F. John et al., "Continuous Patient Monitoring with a Small Digital Computer," *Computers and Biomedical Research*, vol. 5, Abstract only, 1972, Retrieved online from: Neonatology on the Web.
Leyerle, Beverley J. et al., "Integrated Computerized Databases for Medical Data Management Beyond the Bedside" *International Journal of Clinical Monitoring and Computing*, vol. 7, 1990, pp. 83-89.
Leyerle, Beverley J. et al., "The PDMS as a Focal Point for Distributed Patient Data." *International Journal of Clinical Monitoring and Computing*, vol. 5, 1988. pp. 155-161.
Li, Xin et al., "A World Wide Web Telemedicine System" *SPIE*, vol. 2711, 1996; pp. 427-439.
Litt et al. "Graphical representation of medical information in the visual chart" Proceedings, 1994 IEEE Seventh Symposium on Computer-based Medical Systems, pp. 252-257, Jun. 11-12, 1994.
M. de Beer, N. A. et al., "Clinical Evaluation of a Method for Automatic Detection and Removal of Artifacts in Auditory Evoked Potential Monitoring." *J. Clinical Monitoring*, vol. 11, No. 6, Nov. 1995: 381-391.
Mabry, Susan L. et al., Integrated Medical Analysis System, Proceedings of the 1997 Winter Simlation Conference, 1997, pp. 1167-1168.
Major, Kevin et al., "Wireless Clinical Alerts and Patient Outcomes in the Surgical Intensive Care Unit." *The American Surgeon*, vol. 68, Dec. 2002; pp. 1057-1060.
Makivirta, A. & E. M. J. Koski, "Alarm-Inducing Variability in Cardiac Postoperative Data and the Effects of Prealarm Delay." *Critical Care Medicine*, vol. 8, No. 6, May 1994: 153-162.
Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.
Martin, J. F., "Closed-Loop Control of Arterial Pressure During Cardiac Surgery." *J. Clinical Monitoring*, vol. 8, No. 3, Jul. 1992: 252-253.
McDonald, CJ, "Protocol-Based Computer Reminders, the Quality of Care and the Non-Perfectibility of Man," *The New England Journal of Medicine*, vol. 295, No. 24, Abstract only, Dec. 9, 1976, Retrieved online from: Science Library.
McDonald, Clement J. and William M. Tierney, "Computer-Stored Medical Records, Their Future Role in Medical Practice," JAMA, vol. 259, No. 23, pp. 3433-3440; Jun. 17, 1988.
Merz, U. et al., "Computer-Assisted Monitoring in the Neonatal Intensive Care Unit [German]," *Klin Padiatr*, vol. 207, No. 6, Abstract only, Nov./Dec. 1995, Retrieved online from: Neonatology on the Web.
Metnitz, P.G. et al., "Computer Assisted Data Analysis in Intensive Care: the ICDEV Project—Development of a Scientific Database System for Intensive Care (Intensive Care Data Evaluation Project)" *Int J Clin Monit Comput*, vol. 12, No. 3, Abstract only, 1995, Retrieved online from: Neonatology on the Web.
Meyer, C., "Visions of Tomorrow's ICU." *American J. Nursing*, Apr. 1993: 27-31.

Microsoft Press Computer Dictionary, Third Edition, 1997, p. 430.
Microsoft Support Document 236963 describing the functionality of the Windows 95 OS.
Miksch, Silvia. Artificial Intelligence for Decision Support: Needs Possibilities, and Limitations in ICU, 10$^{th}$ Postgraduate Course in Critical Care Medicine APICE '95, Springer, 1995.
Miller, Randolph A. et al., "Summary Recommendation for Responsible Monitoring and Regulation of Clinical Software Systems," *Annals of Internal Medicine*, vol. 127, No. 9, pp. 842-845, Nov. 1, 1997.
Morales, A. Alfredo et al., "An Application Server Approach for Integration of Clinical Systems," *Proceedings of the AMIA 1999 Annual Symposium*, Abstract only, AMIA, 1999, Retrieved online from: Neonatology on the Web.
Mrus, Joseph M., "Getting Beyond Diagnostic Accuracy: Moving toward Approaches That Can be Used in Practice" *CID*, Editorial Commentary, vol. 38, May 15, 2004; pp. 1391-1393.
Nelson, Russell M. et al., "Computer Based Monitoring of Patients Following Cardiac Surgery" *Computers in Cardiology*, vol. 5, No. 4, Jul.-Aug. 1969; pp. 926-930.
Nenov, V. I. et al., "Computer Applications in the Intensive Care Unit." *Neurosurgery Clinics of North America*, vol. 5, No. 4, Oct. 1994: 811-827.
Nenov, Valeriy et al. Remote Access to Neurosurgical ICU Physiological Data using the World Wide Web, Health Care in the Information Age, 1996, pp. 242-249.
Nobel, J. J., "Physiologic Monitoring Systems, Acute Care." *Pediatric Emergency Care*, vol. 8, No. 4, Aug. 1992: 235-237.
Norris, Patrick R. et al., "Web-Based Data Integration and Annotation in the Intensive Care Unit." Proc AMIA Annu Fall Symp. 1997; pp. 794-798.
Nossister. Using Excel 5 for Windows (The User Friendly Reference), Copyright 1995, by Que Corporation.
Oliver, Suzanne, "Take Two Aspirin; The Computer will Call in the Morning." *Forbes*, Mar. 14, 1994. pp. 110-111.
On, J. A. & Westenskow, D. R., "A Breathing Circuit Alarm System Based on Neural Networks." *J. Clinical Monitoring*, vol. 10, No. 2, Mar. 1994: 101-109.
Palley, N. A., et al. "Programming in the Medical Real-Time Environment." *AFIPS Conference Proceedings*, vol. 37, *Fall Joint Computer Conference*, Nov. 17-19, 1970, Houston Texas. pp. 589-598.
Pryor, T. Allan et al., "HELP —A Hospital—Wide System for Computer-Based Support of Decision-Making" pp. 1-14 (unnumbered).
Pryor, T. Allan et al., "HELP —A Total Hospital Information System" Proceedings of the Fourth Annual Symposium on Computer Applications in Medical Care, Part I, Nov. 2-5, 1980, Washington, D.C.; pp. 3-7.
PTO Decision on Re-examination for Patent No. 6,804,656.
Reddy, Dr. Ramana & Dr. V. "Juggy" Jagannathan, "Final Report" *Secure Collaboration for Technology for Rural Clinical Telemedicine*, Contract No. N01-LM-6-3549, Submitted by: West Virginia Research Corporation, Concurrent Engineering Research Center, West Virginia University, Morgantown, WV, Submitted to: The National Library of Medicine, Copyright © 1999 West Virginia University; pp. 1-77.
Reddy, Dr. Ramana & Dr. V. "Juggy" Jagannathan, "Project Summary; Telemedicine Team" *Secure Collaboration for Technology for Rural Clinical Telemedicine*, Funded by the National Library of Medicine, Copyright © 1999 West Virginia University; Retrieved from Internet, pp. 1-12.
Remote Monitoring of ICU Patients Lowers Mortality Rates, Complications, Johns Hopkins Newsrelease, Mar. 20, 2001, http://www.newswise.com/areticles/2001/3/ICU.JHM.html.
Reddy, S. et al., "Experiences with ARTEMIS—An Internet-Based Telemedicine System" 1997 AMIA, Inc.; pp. 759-763.
Rind, David M. et al., "Designing Studies of Computer-Based Alerts and Reminders," *M.D. Computing*, vol. 12, No. 2, Abstract only, 1995, Retrieved online from: Neonatology on the Web.
Rind, David M., et al., "Effect of Computer-Based Alerts on the Treatment and Outcomes of Hospitalized Patients," *Archives of Internal Medicine*, Vo. 154, Jul. 11, 1994, pp. 1511-1517.

(56) References Cited

OTHER PUBLICATIONS

Rocha, Beatriz H.S.C. et al., "Computerized Detection of Nosocomial Infections in Newborns," In Symposium on Computer Applications in Medical Care, Nov. 5-9, 1994, Washington, DC; pp. 684-688.

Rosenfeld, M.D., Brian A. FCCM, FCCP, et al., Intensive care unit telemedicine: Alternate paradigm for providing continuous intensivist care, Critical Care Medicine, vol. 28, No. 12, 2000 p. 3925.

Runciman, W. B. et al., "The Pulse Oximeter: Applications and Limitations—An Analysis of 2000 Incident Reports." *Anaesthesia and Intensive Care*, vol. 21, No. 5, Oct. 1993: 543-550.

Safran, Charles et al., "Computer-Based Support for Clinical Decision Making," *M.D. Computing*, vol. 7, No. 5, Abstract only, 1990, Retrieved online from: Neonatology on the Web.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Seiver, Adam, "ICU Bedside Technology, Critical Care Computing, Past, Present, and Future" *Critical Care Clinics*, vol. 16, No. 4, Oct. 2000; pp. 1-17. Retrieved from Internet on Oct. 13, 2003.

Shabot, M. M. et al., "Decision Support Alerts for Clinical Laboratory and Blood Gas Data" *International Journal of Clinical Monitoring and Computing*, vol. 7, 1990, pp. 27-31.

Shabot, M. Michael & Reed M. Gardner, "Decision Support Systems in Critical Care." *Computers and Medicine*, Springer-Verlag New York Inc., 1994; pp. 1-419.

Shabot, M. Michael and Mark LoBue, "Cedars-Sinai Medical Center Critical Alerting System" Cedars-Sinai Medical Center, Feb. 2004; pp. 1-16.

Shabot, M. Michael and Mark LoBue, "Real-Time Wireless Decision Support Alerts on a Palmtop PDA" 1995 AMIA, Inc., pp. 174-177.

Shabot, M. Michael et al., "Inferencing Strategies for Automated ALERTS on Critically Abnormal Laboratory and Blood Gas Data" 1989 SCAMC, Inc.; pp. 54-57.

Shabot, Michael M. et al., "Automatic Extraction of Intensity-Intervention Scores From a Computerized Surgical Intensive Care Unit Flowsheet" *The American Journal of Surgery*, vol. 154, Jul. 1987; pp. 72-78.

Shabot, Michael M. et al., "Wireless Clinical Alerts for Physiologic, Laboratory and Medication Data" Proceedings of the American Medical Informatics Association Anuual Symposium, 2000; pp. 789-793.

Shortliffe, Edward H., "Computer Programs to Support Clinical Decision Making," *JAMA*, vol. 258, No. 1, Abstract only, Jul. 3, 1987, Retrieved online from: Neonatology on the Web.

Sima, Chaoxin et al., "Vital Signs Services for Secure Telemedicine Applications" Proc AMIA Symp 1998: pp. 361-365.

Simon Project (Signal Interpretation and Monitoring), Vanderbilt University, Nashville, TN. Copyright © 2004 by Vanderbilt Universtiy, Retrieved from Internet: Page last modified Aug. 24, 2004, pp. 1-20.

Simpson, R. L., "Automating the ICU: Facing the Realities." *Nursing Management*, vol. 23, No. 3, Mar. 1992: 24-26.

Sipkoff, Martin, "Systems Aid Rural Health Delivery," Published by Premier Healthcare Resource Inc., Sep. 2003, pp. 1-4. Retrieved online from: QIPhysician.com.

Sittig, D. F. & M. Factor, "Physiologic Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Sittig, D. F. et al., "COMPAS: A Computerized Patient Advice System to Direct Ventilatory Care" Conference of Medical Informatics 88: Computers in Clinical Medicine, Institute of Measurement and Control for the British Medical Informatics Society, Nottingham, UK, Sep. 13-15, 1988; pp. 251-256.

Sittig, Dean F. et al., "Clinical Evaluation of Computer-Based Respiratory Care Algorithms" *International Journal of Clinical Monitoring and Computing*, vol. 7, 1990; pp. 177-185.

Sittig, Dean F. et al., "Computerized Management of Patient Care in a Complex, Controlled Clinical Trial in the Intensive Care Unit." *Computer Methods and Programs in Biomedicine*, vol. 30, 1989; pp. 77-84.

Sittig, Dean F. et al., "Computerized Screening for Identification of Adult Respiratory Distress Syndrome (ARDS) Patients" 1988 SCAMC, Inc., pp. 698-702.

Sittig, Dean F. et al., "Implementation of a Computerized Patient Advice System Using the HELP Clinical Information System" *Computers and Biomedical Research*, vol. 22, 1989; pp. 474-487.

Snowden, S. et al., "An Expert System to Assist Neonatal Intensive Care," *J Med Eng Technol*, vol. 21, No. 2, Abstract only, Mar./Apr. 1997, Retrieved online from: Neonatology on the Web.

Stewart. "Patenting of Software—Proposed Guidelines and the Magic Dividing Line that disappeared". JPTOS, pp. 681-698, Sep. 1995.

Stoodley, K. D. C. et al., "Problems in the Development of a Computerized Ward Monitoring System for a Pediatric Intensive Care Unit." *International J. Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Tate, Karen E. et al., "Nurses, Pagers, and Patient-Specific Criteria: Three Keys to Improved Critical Value Reporting" 1995 AMIA, Inc.; pp. 164-168.

Uckun, S., "Intelligent Systems in Patient Monitoring and Therapy Management." *International J. Clinical Monitoring and Computing*, vol. 11, 1994: 241-253.

Visicu/Cerner Complaint for Patent No. 6,804,656.

Warner, Homer R. et al., "Computer-based Monitoring of Cardiovascular Functions in Postoperative Patients" *Supplement II to Circulation*, vols. XXXVII and XXXVIII, Apr. 1968; pp. II-68 to II-74.

Weil, Max H., "Use of Automated Techniques in the Management of the Critically Ill," *Hospital Information Systems*, Marcel Dekker, Inc., 1972, 333-381.

West Virginia University Research Corporation, Secure Collaboration Technology for Rural Clinical Telemedicine: Final Report, National Library of Medicine.

Westenkow, Dwayne R., "Automating Patient Care with Closed-Loop Control," *M.D. Computing*, vol. 3, No. 2, Abstract only, 1986, Retrieved online from: Neonatology on the Web.

Whiting, R and L. Hayes, "The Practice of Telemedicine—the TARDIS Perspective" *Informatics in Healthcare*—Australia, vol. 6, No. 3, Jul./Aug. 1997; pp. 103-106.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Young, W. Hsueh-fen et al., "Computerized Ventilator Data Selection: Artifact Rejection and Data Reduction," *International Journal of Clinical Monitoring and Computing*, vol. 14, May 5, 1997: 165-176.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Transaction History, for U.S. Appl. No. 09/946,421, dated May 29, 2009.

Transaction History, for U.S. Appl. No. 09/946,304, dated May 29, 2009.

Transaction History, for U.S. Appl. No. 09/946,274, dated May 29, 2009.

Transaction History, for U.S. Appl. No. 10/985,950, dated May 29, 2009.

(56) References Cited

OTHER PUBLICATIONS

Transaction History, for U.S. Appl. No. 09/341,065, dated May 29, 2009.
Transaction History, for U.S. Appl. No. 90/007,927, dated May 29, 2009.
Transaction History, for U.S. Appl. No. 11/474,017, dated May 29, 2009.
Transaction History, for U.S. Appl. No. 10/355,527, dated May 29, 2009.
Transaction History, for U.S. Appl. No. 11/031,125, dated May 29, 2009.
Transaction History, for U.S. Appl. No. 09/443,072, dated May 29, 2009.
Transaction History, for U.S. Appl. No. 90/007,377, dated May 29, 2009.
Transaction History, for U.S. Appl. No. 90/008,276, dated May 29, 2009.
Transaction History, for U.S. Appl. No. 10/355,435, dated May 29, 2009.
Non-final Office Action issued in U.S. Appl. No. 11/474,017, dated Mar. 31, 2010, 35 pages.
Non-final Office Action issued in U.S. Appl. No. 10/985,950, dated May 14, 2010, 16 pages.
Non-final Office Action issued in U.S. Appl. No. 09/946,304, dated May 18, 2010, 15 pages.
Notification of Transmittal of the International Search Report and the Written Opinion of the International Searching Authority, or the Declaration for Application No. PCT/IB05/00646, dated Nov. 13, 2007, 9 pages.
Supplementary European Search Report for Application No. 05708735.5, dated Nov. 13, 2008, 4 pages.
Ouzzani, M. et al., "Ontological Approach for Information Discovery in Internet Databases." Distributed and Parallel Databases, 8, 2000, pp. 367-392.
Nenov, Valeriy et al., "Remote Analysis of Physiological Data from Neurosurgical ICU Patients," Application of Information Technology, Feb. 12, 1996, 3:318-327.
Bailes, Julian, "NeuroLink: A Neurosurgical Wide-Area Computer Network," Neurosurgery, vol. 35(4), Oct. 1994, pp. 732-736.
Pryor, Allan et al. Help-a hospital-wide system for computer-based support of decision-making. Proceedings of the 14th Annual Hawaii International Conference on Systems Sciences; Jan. 8, 1981.
Visicu/Cerner Complaint for Patent No. 6,804,656, filed Nov. 12, 2004.
West Virginia University Research Corporation, Secure Collaboration Technology for Rural Clinical Telemedicine: Final Report, National Library of Medicine, included as part of a CD containing proceedings of the National Library of Medicine symposium that took place on Mar. 13, 2001.
Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.
Perednia, Douglas A. Telemedine Technology and Clinical Applications, JAMA, vol. 6, Feb. 8, 1995, p. 483.
Perlstein, Paul H. et al., "Computer Assisted Newborn Intensive Care," *Pediatrics*, vol. 57, No. 4, Abstract only, Apr. 1976, Retrieved online from: Neonatology on the Web.
Pestotnik, Stanley L. et al., "Therapeutic Antibiotic Monitoring: Surveillance Using a Computerized Expert System" *The American Journal of Medicine*, vol. 88, 1990; pp. 43-48.
Pryor, T. A. et al., "The Help System" 1982 IEEE, pp. 19-27.
Pryor, T. A. et al., "The HELP System" *Journal of Medical Systems*, vol. 7, No. 2, 1983; pp. 87-102.
Pryor, T. Allan et al., "A Distributed Processing System for Patient Management" 1978 IEEE, *Computers in Cardiology*, Sep. 1978; pp. 325-328.
Pryor, T. Allan et al., "Computer System for Research and Clinical Application to Medicine" Fall Joint Computer Conference, 1968; Reprinted from AFIPS—Conference Proceedings, vol. 33, 1968; pp. 809-816.
Pryor, T. Allan et al., "HELP—A Total Hospital Information System" Proceedings of the Fourth Annual Symposium on Computer Applications in Medical Care, Part I, Nov. 2-5, 1980, Washington, D.C.; pp. 3-7.
PTO Decision on Re-examination for Patent No. 6,804,656, Oct. 12, 2004.
Rampil, I. J., "Intelligent Detection of Artifact." *The Automated Anesthesia Record and Alarm Systems*, Chapter 17, 1987: 175-190.
Reddy, Dr. Ramana & Dr. V. "Juggy" Jagannathan, "Final Report" *Secure Collaboration for Technology for Rural Clinical Telemedicine*, Contract No. N01-LM-6-3549, Submitted by: West. Virginia Research Corporation, Concurrent Engineering Research Center, West Virginia University, Morgantown, WV, Submitted to: The National Library of Medicine, Copyright © 1999 West Virginia University; pp. 1-77.
Reddy, Dr. Ramana & Dr. V. "Juggy" Jagannathan, "Phase 1 Quarterly Report, Apr. 1-Jun. 30, 1997" *Secure Collaboration for Technology for Rural Clinical Telemedicine*, Funded by the National Library of Medicine, Copyright © 1999 West Virginia University; Retrieved from Internet, pp. 1-5.
Reddy, Dr. Ramana & Dr. V. "Juggy" Jagannathan, "Phase 1 Quarterly Report, Jan. 1-Mar. 1, 1997" *Secure Collaboration for Technology for Rural Clinical Telemedicine*, Funded by the National Library of Medicine, Copyright © 1999 West Virginia University; Retrieved from Internet, pp. 1-5.
Reddy, Dr. Ramana & Dr. V. "Juggy" Jagannathan, "Phase 1 Quarterly Report, Sep. 1-Dec. 1, 1996" *Secure Collaboration for Technology for Rural Clinical Telemedicine*, Funded by the National Library of Medicine, Copyright © 1999 West Virginia University; Retrieved from Internet, pp. 1-5.
Tate, Karen E. And Reed M. Gardner, "Computers, Quality, and the Clinical Laboratory: A Look at Critical Value Reporting" Seventeenth Annual Symposium on Computer Applications in Medical Care, Oct. 30-Nov. 3, 1993, Washington D.C.; pp. 193-197.
Tate, Karen E. et al., "A Computerized Laboratory Alerting System" *M.D. Computing*, vol. 7, No. 5, 1990; pp. 296-301.
Tate, Karen E. et al., "Nurses, Pagers, and Patient-Specific Criteria: Three Keys to Improved Critical Value Reporting" 1995 AMIA, Inc.; pp. 164 —168.
Thomas, Karl W. et al., "Evolution of Internet-Based Clinical Decision Support Systems," Journal of Medical Internet Research 1999; 1(2): e6 <URL: http//www.jmir.org/1999/2/e6/>, pp. 1-12.
Tobin, Martin, "Principles and Practice of Intensive Care Monitoring" McGraw-Hill, Inc., United States of America, 1998 (pp. 1-172 and pp. 1329-1407).
Tsien, Christine L. "Reducing False Alarms in the Intensive Care Unit: A Systematic Comparison of Four Algorithms" Proceedings Annual Amia Fall Symposium (Paper on CD-ROM) 1997.
Tsien, Christine L. "Reducing False Alarms in the Intensive Care Unit: A Systematic Comparison of Four Algorithms" Proceedings Annual AMIA Fall Symposium (1997), p. 894.
Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.
Tsien, Christine L. And James Fackler, "Poor Prognosis for Existing Monitors in the Intensive Care Unit" *Critical Care Medicine*, vol. 25, No. 4, 1997: 614-619.
Tsien, Christine L., "TrendFinder: Automated Detection of Alarmable Trends", Department of Electrical Engineering and Computer Science, Massachusetts Institute of Technology, Massachusetts; Jun. 2000.
Tsien, Christine L.. "Reducing False Alarms in the Intensive Care Unit: A Systematic Comparison of Four Algorithms" Proceedings *AMIA* Symposium, 1997. pp. 9-14 (unnumbered).
Uckun, S., "Intelligent Systems in Patient Monitoring and Therapy Management." *International J Clinical Monitoring and Computing*, vol. 11, 1994: 241-253.

(56) References Cited

OTHER PUBLICATIONS

"Vital Signs," http://en.wikipedia.org/wiki/Vital-signs (accessed on Jun. 9, 2010), 5 pages.

Wang, Kang et al., "A Real Time Patient Monitoring System on the World Wide Web," *Proceedings of the 1996 AMIA Annual Fall Symposium*, Abstract only, Hanley and Belfus, Inc., Nov. 1996, Retrieved online from: Neonatology on the Web.

Warner, Homer R. et al., "Computer-based Monitoring of Cardiovascular Functions in Postoperative Patients" *Supplement II to Circulation*, vols. XXXVII and XXXVIII, Apr. 1968; pp. 11-68 to 11-74.

Webb, R. K., "Medical Decision Making and Decision Analysis." Anesthesia and Intensive Care, vol. 16, No. 1, Feb. 1988: 107-109.

Weil, Max H., "Use of Automated Techniques in the Management of the Critically Ill," *Hospital Information Systems*, Marcel Dekker, Inc., 1972, 333-381.

\* cited by examiner

MONITORING PATIENT CONDITIONS

CROSS REFERENCE TO RELATED APPLICATIONS

Pursuant to 35 USC §119(e), this application claims the benefit of prior U.S. Provisional Application 61/092,527, filed Aug. 28, 2008. The application is incorporated by reference in its entirety.

BACKGROUND

This description relates to monitoring patient conditions to provide intensive care services within and external to intensive care units.

Medical monitoring equipment is located in a variety of healthcare facilities. One facility that may contain such equipment can be an intensive care unit (ICU) that allows patients in critical condition to be monitored. In general, an ICU is a specialized section of a healthcare facility (e.g., a hospital) and is equipped with the state-of-the-art electronic medical devices and a dedicated medical staff so that comprehensive and continuous care can be provided to patients with potentially life-threatening conditions. The use of the medical equipment in the ICUs can incur significant financial costs and the maintenance of the equipment may similarly call for significant fees.

SUMMARY

In general, in one aspect, a computer implemented method for monitoring patients released from an intensive care unit in a healthcare environment is described. The method comprises receiving medical information of a patient located at a location different from the intensive care unit, evaluating conditions of the patient by applying one or more rules to the medical information of the patient, and sending a message to the intensive care unit when the conditions of the patient match the one or more rules.

Implementations may include one or more of the following features. The patient at the location is monitored using a clinical medical device. The patient's location is determined using an electronic device. The electronic device is integrated with a device collecting the medical information of the patient at the location. The electronic device comprises a portable electronic device. Medical information of the patient is stored in a centralized data repository; and providing users at the intensive care unit with access to the centralized data repository. A user is authenticated when the user requests to access the centralized data repository. The medical information of the patient is updated in the centralized data repository. The one or more rules in connection with the medical information are updated. Treatment recommendations are provided to users at the location or at the intensive care unit. The conditions of the patient are displayed in the intensive care unit continuously.

In general, in another aspect, a computer-readable medium for storing instructions that are executable by a computer is described. The execution of the instructions causes the computer to receive medical information of a patient located in at a location different from an intensive care unit, evaluate conditions of the patient by applying one or more rules to the patient information of the patient, and send a message to the intensive care unit when the conditions of the patient match the one or more of the rules.

Implementations may include one or more of the following features. The computer monitors the patient at the location using a clinical medical device. The computer to determines the patient's location using a electronic device. The electronic device is integrated with a device collecting the medical information of the patient at the location. The electronic device comprises a portable electronic device. The computer stores medical information of the patient in a centralized data repository and provided users at the intensive care unit with access to the centralized data repository. The computer authenticates a user when the user requests to access the centralized data repository. The computer updates the medical information of the patient in the centralized data repository and updates the one or more rules in connection with the medical information. The computer provides treatment recommendations to users at the location or at the intensive care unit. The computer displays the conditions of the patient in the intensive care unit continuously.

In general, in another aspect, a system comprises a computing device comprising a memory and an engine. The engine is for receiving medical information of a patient located at a location different from an intensive care unit, evaluating conditions of the patient by applying one or more rules to the medical information of the patient, and sending a message to the intensive care unit when the conditions of the patient match the one or more rules.

Implementations may include one or more of the following features. The medical information is obtained by monitoring the patient at the location using a clinical medical device. The medical information comprises information about the patient's location determined by an electronic device. The electronic device is integrated with a device collecting the medical information of the patient at the location. The electronic device comprises a portable electronic device. The memory comprises a centralized data repository for storing medical information of the patient and the computer provides users at the intensive care unit with access to the centralized data repository. The computer authenticates a user when the user requests to access the centralized data repository. The engine updates the medical information of the patient in the centralized data repository and the one or more rules in connection with the medical information. The engine is configured to provide treatment recommendations to users at the location or at the intensive care unit. Conditions of the patient is displayed by a display in the intensive care unit continuously.

The details of one or more examples are set forth in the accompanying drawings and the description below. Further features, aspects, and advantages are apparent in the description, the drawings, and the claims.

DETAILED DESCRIPTION

Figure 1:
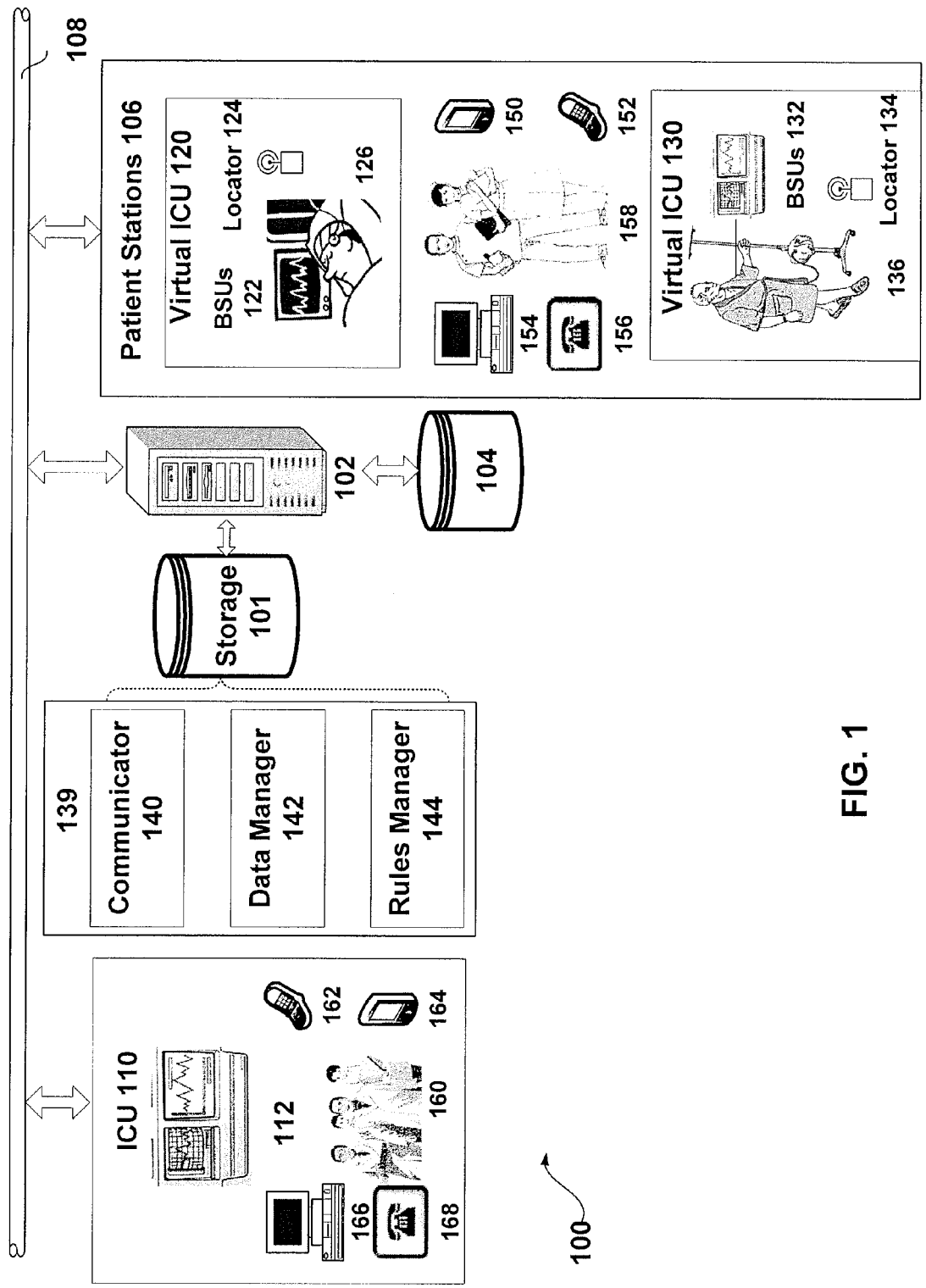
FIG. 1 illustrates an exemplary monitoring system for a network-integrated intensive care unit (NI-ICU).

Referring to FIG. 1, a medical information system 100 includes one or more computer devices, such as general-purpose personal computers, personal digital assistants, specialized computing devices, or reading machines. The computer devices collect various types of medical information at multiple locations (e.g., patient locations) and exchange the collected information over a shared network 108. The medical information can be processed by manager software stored on a patient specific rules engine 144, and can be displayed at an ICU station 110 of a healthcare facility. In this arrangement, some patients (e.g., patient 126) that are considered relatively healthy may be released from the ICU station 110 and are remotely monitored by medical professionals 160 at the ICU station 110. Medical information (e.g., monitoring equipment readouts) of these patients may be collected, for example, in real time and processed by a patient specific rules engine 144 and other associated software. Patient conditions may be monitored and identified as needed, and messages (e.g., alert messages) may be sent to medical professionals 160, 158 located proximate or external to the ICU station 110 to act on the conditions of the patient 126 (e.g., a message is issued to prompt intervention).

By allowing medical information to be collected from sites external to the ICU station 110, a network-integrated healthcare facility is produced. Through such a network, resources, e.g., equipment and medical professionals 160, at the ICU are efficient used and conserved. Cost of care for patients (e.g., patient 126) and equipment related cost may be reduced. In one arrangement, the ICU station 110 can be located within a healthcare facility (e.g., a hospital) and external patient stations 106 (e.g., to which the patient 126 is moved) may be linked to the ICU station 110 within the medical information system 100. The healthcare professionals 160 at the ICU station 110 can monitor patients released from the ICU station 110 independent of the patients' current locations. Effectively, virtual ICUs 120, 130 are generated in the patient stations 106 external to the ICU 110. Through connections via the network 108, the ICU 110 and the virtual ICUs 120, 130 may be considered to have formed an NI-ICU system. More ICUs or virtual ICUs (not shown) can be included in the NI-ICU system. One or more NI-ICU systems may also be generated within the hospital. In each ICU or virtual ICU of the NI-ICU system, one or more patients may be connected to a variety of clinical devices within bedside units (BSUs) 122, 132 that collect measurement data, e.g., in real time, from the respective patient or patients. Examples of the clinical devices include respirators, blood pressure monitoring device, electrocardiographs, or other suitable devices. Various operations may be executed upon the collected data, for example, patient data collected by the clinical devices can be stored in one or more data structures (e.g., a database) for examination and/or later use. Numerous techniques and methodologies may be implemented to collect, process and distribute the medical information represented by the patient data.

The BSUs 122, 132 can also receive input by the medical professionals 160, 158 and display the input. For example, the input can be associated with observations, notes, orders, and the like. Each clinical device of the BSUs 122, 132 can be connected with a display system, e.g., including a universal interface device for facilitating information input and output. In one arrangement, the universal interface device is an RS-232 interface.

In some implementations, an operating system, such as Microsoft Windows®, is implemented in the BSUs 122, 132 to provide a user-friendly interface for a user to access and input or retrieve patient medical information. Patients in each NI-ICU (e.g., located in an ICU or virtual ICU of the NI-ICU system) may equipped with locators (e.g., locators 124, 134).

In some instances the locators may be positioned on structures associated with the location of the patients (e.g., wall mounted). The locators may provide real-time geographic information of the patient 126, 136, e.g., the hospital ward, examination room, floor or wing that the patient is presently located, to the BSUs 122, 132, and the ICU 110, virtual ICUs 120, 130. The patient locators 124, 134 may be integrated into the BSUs 122, 132, respectively, or installed separately as portable devices for the patient to carry around inside or outside a hospital.

The NI-ICUs 110, 120, 130 and the devices, such as the locators 124, 134 enables the patients at different recovery stages to have some freedom of movement. For example, a fully ambulatory patient equipped with a locator can be allowed to exercise, e.g., walk, within an area designated by a physician. Furthermore, the locators 124, 134 also enable continuous monitoring of patients in transit, e.g., during which the patient is moved among different examining rooms. Various location tracking technologies can be used for monitoring patient location in real time (e.g., a portable electronic Global Positioning System (GPS) tracker.)

Patient information collected in each NI-ICU 120, 130, such as information from measurements in the BSUs and/or patient locations, may be saved locally in the BSUs or remotely in one or more central storage devices (not shown).

In some implementations, the network 108 can be a wired and/or wireless distributed computing network. The network 108 can transmit the patient information among the NI-ICU 120, 130 and a computer system 102 (or a centralized server 102). The centralized server 102 may include a storage 101 for storing a computer program product 139 to manage a NI-ICU system. In addition, the centralized server 102 can also include a database storage 104, e.g., a computer storage medium, for example, magnetic or optical disk storage, or non-volatile semiconductor memory storage. The centralized server 102 can also provide an interface shared by multiple units in the healthcare facility (e.g., the hospital). Each NI-ICU 120, 130 may continuously monitor the reliability of its link to the network 108 via a network interface. In the event of a network failure, patient medical information or data can be replicated at the server 102 and the local NI-ICUs to reduce the probability of losing information.

In one arrangement, the computer program product 139 may include instructions, such that when executed, the centralized server 102 performs functions of a communicator 140. The communicator 140 operates, e.g., to specify a user communication protocol for the user's hardware, operating system, line configuration, etc. For example, the communicator 140 can specify an appropriate communication port, speed (baud rate), interrupt settings, modem type and control strings, dial prefix, pulse or tone, and call waiting/shut-off for a standard duplex communication of telephone/audio connection 156, 168 (in the ICU 110). The communicator 140 can maintain a reliable connection among the NI-ICUs 110, 120, 130. In some arrangements, other types of wide bandwidth, high speed communication capabilities, e.g., wired and wireless (e.g., satellite communications), may be implemented in the NI-ICU system.

The centralized server 102 also includes a data manager software 142 that may provide different users the ability to manage the patient medical information and data stored on the database storage 104. The data manager software 142 also allows users to process resources (e.g., information from equipment) and control equipment through multiple user logic views at different locations (e.g., different terminals). The data manager software 142 also allows users (e.g., authorized users) to access the database storage 104 e.g., to analyze and update patient medical information and data. The data manager software 142 may also control and enforce database security by preventing unauthorized users from viewing, accessing and updating the database stored in the database storage 104.

As will be described in more detail below in FIG. 3, the centralized server 102 and the database storage 104 (also referred to as data repository 104) store comprehensive patient records, results from measurements at the BSUs. The centralized server 102 can be configured to allow authorized users to access such information over a network, e.g., the network 108. In some arrangements the server 102 may also channel information to authorized users. Because information associated with the patients and the hospital can be stored in a centralized fashion at the centralized server 102, the medical information system 100 allows simultaneous monitoring and access to the information by multiple users.

In addition, the centralized server 102 also includes the rules manager software 144. The rule manager software 144 evaluates the patient conditions, e.g., continuously, by applying one or more rules. In some implementations, the rules are applied based on the information stored in the centralized server 102 and database storage 104. Implemented as a decision support module, the rules manager software 144 can search for and analyze patterns, values, trends, etc. of the information. The result of the search or analysis can be indicative of clinical deterioration or recovery of the patients and messages can be sent to the healthcare professions 160, 158 (e.g., physicians, nurses, etc.). The messages can be sent to a variety of devices by one or more networks, e.g., the network 108. The devices can include, for example, desktop computers 154, 166, a workstation, a laptop, personal digital assistants (PDAs) 150, 164, cell phones 152, 162, beepers, and other types of network enabled devices and programs, modules or components of such devices. In addition, the messages can also be sent to a console 112 of the ICU station 110. U.S. Pat. No. 6,322,502, incorporated herein by reference in its entirety, describes a medical information system in which data from multiple BSUs is provided to a common database.

The medical team on duty, including the medical professionals 158 may monitor the patients in each NI-ICU and conduct routine medical services and practices. Patient information and physical location (e.g., current location) may also displayed and stored on computer terminals installed at doctor offices and nurse stations.

In some implementations, the centralized console 112 is installed at an ICU 110 to provide the medical personnel 160 with the ability to retrieve multiple step-down NI-ICU patients records from the centralized server 102 and the data depository 104 through the network 108. Current conditions of one or more NI-ICU patients can be displayed, e.g., in an automatic manner and substantially in real-time, on the centralized console 112. The medical professional 160 at the ICU 110 can integrate the data from a plurality of sources to make an informed diagnosis regarding a certain NI-ICU patient. For patient information periodically collected from each NI-ICU, data updates may occur during the review time of medical professional 160. In some implementations, a message may automatically appear on the display screen of the console 112 to inform (e.g., alert) the professional that a particular data set has been updated.

Figure 2:
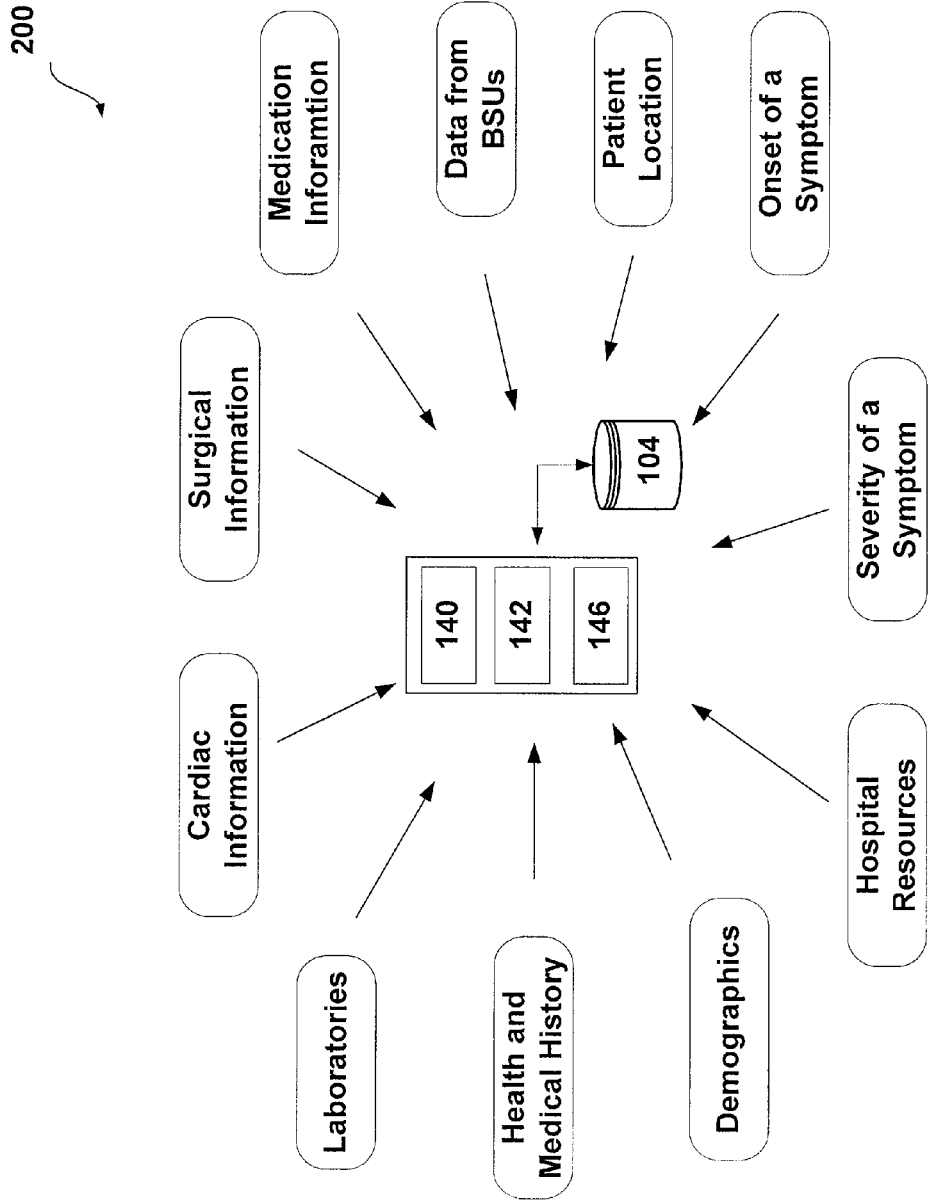
FIG. 2 illustrates exemplary types of information collected and maintained by a monitoring system for an NI-ICU.

Referring to FIG. 2, the communicator 140, the data manager software 142 and the rules manager software 144 that reside on centralized server 102, and database storage 104 are capable of collecting and storing comprehensive patient records transmitted from one or more departments and devices in the healthcare facility (e.g., the hospital). In the illustrated example, the data manager software 142 (shown in FIG. 1) supports organizing, searching, sharing, and synchronizing data along with providing security to the data that resides in the database storage 104. The data management operations may be implemented, for example, based upon a relational data model. In some implementations, specific types of patient data are described in schemas in such a data model, and the data manager software 142 can conveniently and efficiently provide a mechanism to extend the set of schemas to include new types of data defined as subtypes of the corresponding basic type. Updates of the patient data are also monitored and tracked by the medical information system 100. System 100 may also include an application programming interface (API), which enables various application programs to access the data described in the schemas.

In some implementations, a patient's demographics (e.g., patient's name, address, marital status, age, gender, and ethnicity), health and medical history (e.g., illness, allergies, and medications) can be accessed by all the authorized departments and staff of the hospital. Results of laboratory tests and diagnosis (e.g., radiology reports and microbiology reports), cardiac information, surgical information, and medication information may be accessed and updated by physicians or other staff at the hospital. To reduce human errors, the system 100 can provide customized input masks. For example, if a physician inputs patient data that is incorrect, e.g., being incompatible with default information or existing information stored in the system 100, a message appears on a user interface to request the physician to check the input.

Each NI-ICU provides real time measurement data obtained from BSUs 122, 132 (such as electrocardiograph (ECG) data, blood pressure data, pulse rate data, body temperature data, and patient locations) to the centralized data depository 104. Patients and physicians in each NI-ICU 120, 130 can also report abnormal conditions, such as an onset of a symptom, observed by either the patient or a physician. The severity of the symptom is recorded in order for the medical staff on duty in both the ICU station 110 and the patient station 106 to decide whether or not to take immediate action for the patient. Hospital resources may be maintained up-to-date, such that the medical team 160 of the ICU station 110 can order therapies and discuss patient care issues with available specialists and physicians and generate an appropriate treatment plan in a timely fashion.

Figure 3:
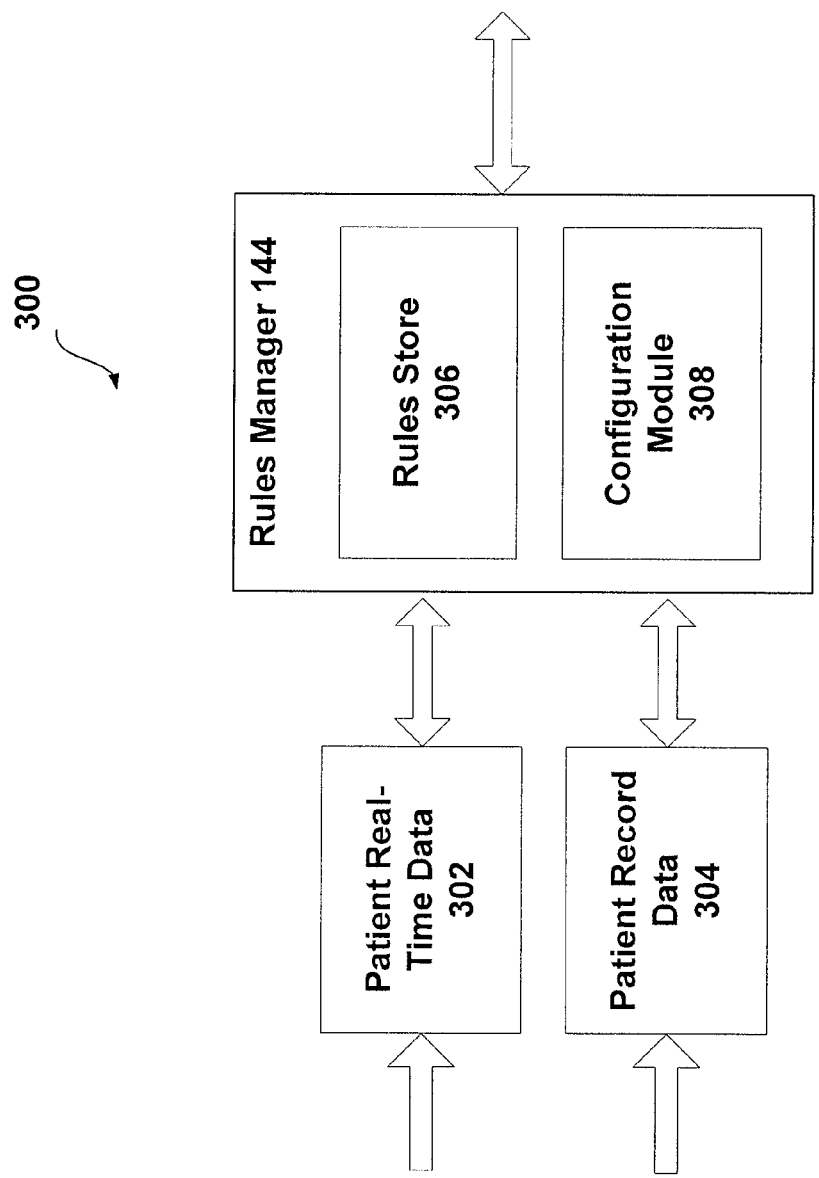
FIG. 3 is illustrates processes executed by a monitoring system for an NI-ICU.

Referring to FIG. 3, the rules manager software 144 includes a rules repository that receives patient measurement data 302 (e.g., real time data) from one or more bedside monitors and patient record data 304 from the sever 102 and centralized database 104. The rules repository contains a rules store 306 that supports general and complex decisions in diagnosis and a configuration module 308 that allows physicians to customize rules for one or more specific patients. For example, by comparing measured data (e.g., from the BSUs 122, 132) to one or more predefined values (e.g., thresholds), the condition of one or more patients may be analyzed by the rules manager software 144 in a continuous or periodic manner. When the condition of a patient deteriorates, e.g., based on results from hemodynamics and respiratory measures, a message (e.g., an alert) to appropriate medical staff may be triggered. The rules store 306 manages parameters, such as values of a threshold for monitoring patient conditions. The threshold can be chosen or determined based on theoretical or empirical data or information of the patient or other patients having similar medical conditions. Healthcare professionals may also generate rules by themselves based on patient con ditions. For example, logical statements and parameters such as:

heart rate>120 bpm and temperature>100 degree may be used in one or more rules in the rules store 306 or configured by the physicians. When the patient conditions satisfy the rules, a message, e.g., including a flag or an alert, may be delivered to ask the physicians to take appropriate actions.

A user interface, such as a graphical user interface (GUI), can be implemented to integrate with the communicator 140 to enable the users (e.g., doctors, nurses) to access, e.g., review and manipulate (e.g., create, delete and modify) the patient information. Such a GUI may also facilitate rule creation, e.g., by displaying to the users a rules template for default rules or threshold values. Some arrangements may provide a rule wizard for creating rules on a step-by step basis.

The rules manager software 144 stores rules that have been created. In some implementations, the name of a person who created the rule and the time the rule is created, the results of the application of the rule are also stored. Invalid or obsolete rules are purged out of the rules module 306 periodically. The rules module 306 can also be updated by authorized users, such as a database administrator. The rules manager software 144 proactively monitors system 100 to provide support to the medical professionals. As such, the system 100 can be configured and administered in accordance with dynamic situations of the patients and multiple departments of the hospital. The system 100 is supported by backups and can maintain and manage dynamic changes in the patient database. Performance of the system 100 can be analyzed and evaluated for adjustment of portions of the system 100, e.g., to improve efficiency or accuracy of the medical care provided to different patients.

Figure 4:
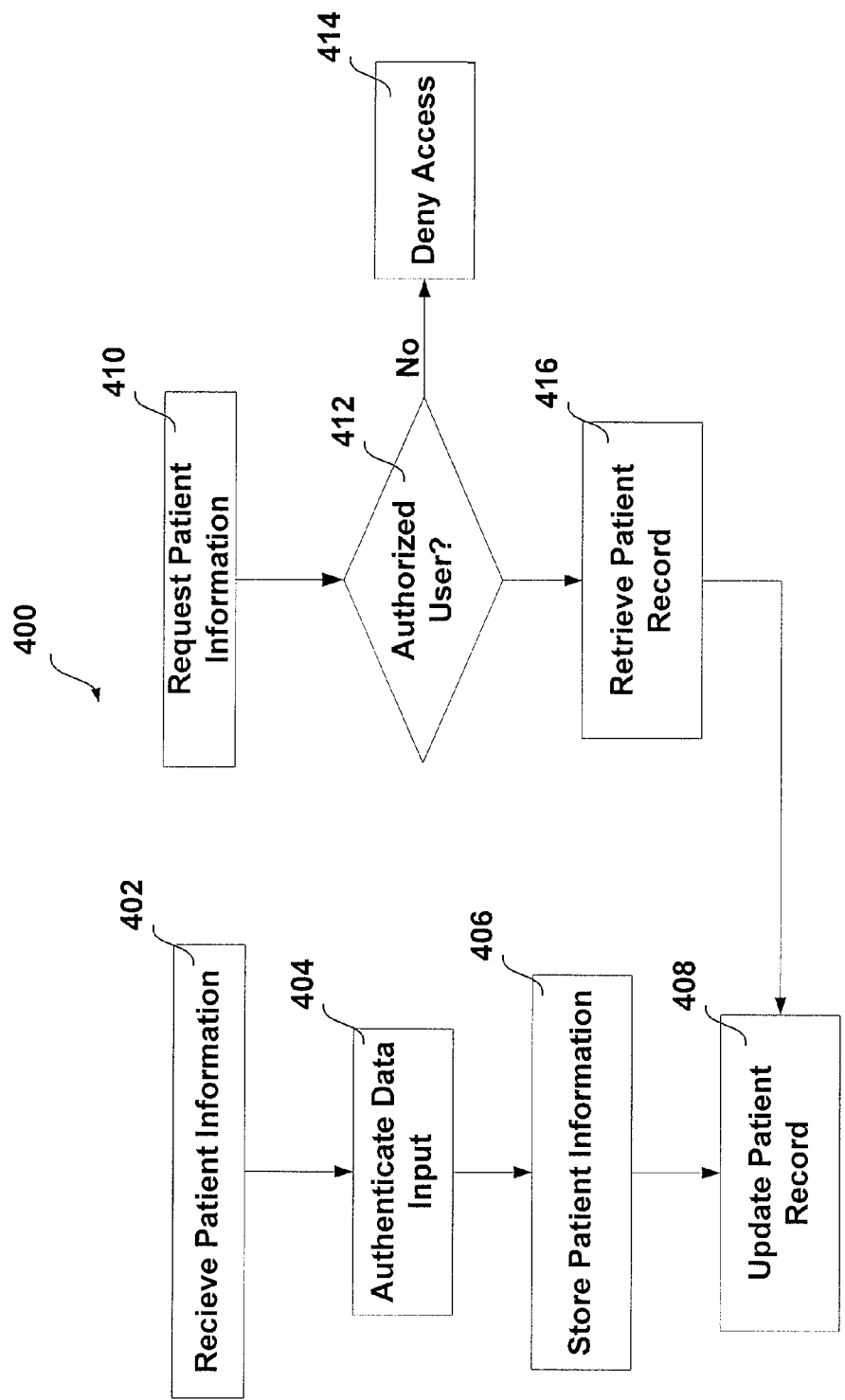
FIG. 4 is a flow chart of operations of a data manager software in a monitoring system for an NI-ICU.

Referring to FIG. 4, a flow chart 400 represents some operations of the data manager software 142 for dynamically maintaining patient information received from one or more sources of a healthcare environment. As mentioned above, the data manager software 142 collects and maintains comprehensive, patient-related information. In some arrangements, upon receiving (402) patient information through the network 108, the data manager software 142 authenticates (404) data input through various mechanisms. In some embodiments, the sources, e.g., a lab or a department of a hospital, of the input data can be checked. For example, usernames, passwords, e.g., one-time passwords, or record biometrics information of the user, e.g., fingerprints, hand geometry, and voice can be checked. In some embodiments, the destinations of the input data can be examined. For example, results of the BSU measurements or patient location information may be reported to certain physicians or departments in a particular format. The authentication process can take the form of checking and confirming special verifiers (e.g., labels or serial numbers) previously assigned to certain devices (e.g., locators 124, 134, BSUs 122, 132). The authentication can also be performed within a particular time window by incorporating timestamps within protocol messages where authentication data is carried. Additionally, other types of information, such as clinical research study information, information related to patient symptoms and diseases, may also be provided to the data manager software 142 from various devices (e.g., a medical content integrated service). In order to enhance the integrity and consistency of system 100, the patient information is categorized and stored (406) in the centralized server 102 and the data depository 104.

In use, the users may need to request (410) specific patient information from the system 100. The users can log into the system 100, e.g., using usernames and passwords. In response to patient information request by healthcare professionals, e.g., 158, 160, the data manager software 142 automatically polls the server 102 and the data depository 104 and determines operations the requesting party is allowed to perform. For example, only doctors are permitted to access and enter information regarding prescriptions for drugs and treatment therapies; and only pharmacists are permitted to access and enter information related to the filling of prescriptions. Nurses and other medical staff are permitted to access and enter information with regards to administration of drugs and treatments. Similarly, user authentication (412) can be performed by various methods, as described above. Unauthorized users or hostile accessing attempts are denied (414) by the system 100. In order to retrieve (416) desired patient records, the data manager software 142 checks or interprets the user request based upon medical knowledge, and subsequently applies appropriate algorithms to search for the records in the data depository 104. Simultaneous editing of same set of patient data may be prohibited by the system 100 in order to maintain the consistency of the patient records. The patient records stored at various locations can be automatically updated 408 when the user updates the records at one of the locations.

The rules manager software 144 can calculate a score representing the severity of a patient's conditions according to user-specified rules. The patient's score reflects relationships between various factors. Each factor can be weighted according to its significance as defined in a formulae used for calculating the score. Members of authorized medical teams in the hospital can define and update the formulae for each patient. The physicians 160 in the ICU 110 can receive messages from the rules manager software 144. Using the received messages and the diagnosis, the physicians can determine whether the treatment of a patient needs to be adjusted. For example, if a patient's complex shows abnormality or an acute condition, an emergency condition service moves the patient from a virtual ICU 120, 130 of the NI-ICU system back to the ICU 110. The resources of the hospital are then reallocated. For example, more devices and physicians can be added, the pharmacy department can be informed for medications, and the specialists can be called in. If the patient conditions become complicated due to persistent symptoms, a symptom assessment service will be launched to better assist the physicians to address the problem. For example, the rules manager software 144 can be adapted to guide the physicians 160 through a series of calculations based on the available patient data to reach a subjective conclusion. If a patient becomes observably healthier, the patient can be routinely examined on a periodic basis, and be discharged from the hospital. Therefore, the NI-ICU system in the hospital can continuously provide patients that have been released from an ICU with high quality and reliable medical services that are usually provided when the patients are in the ICU.

Figure 5:
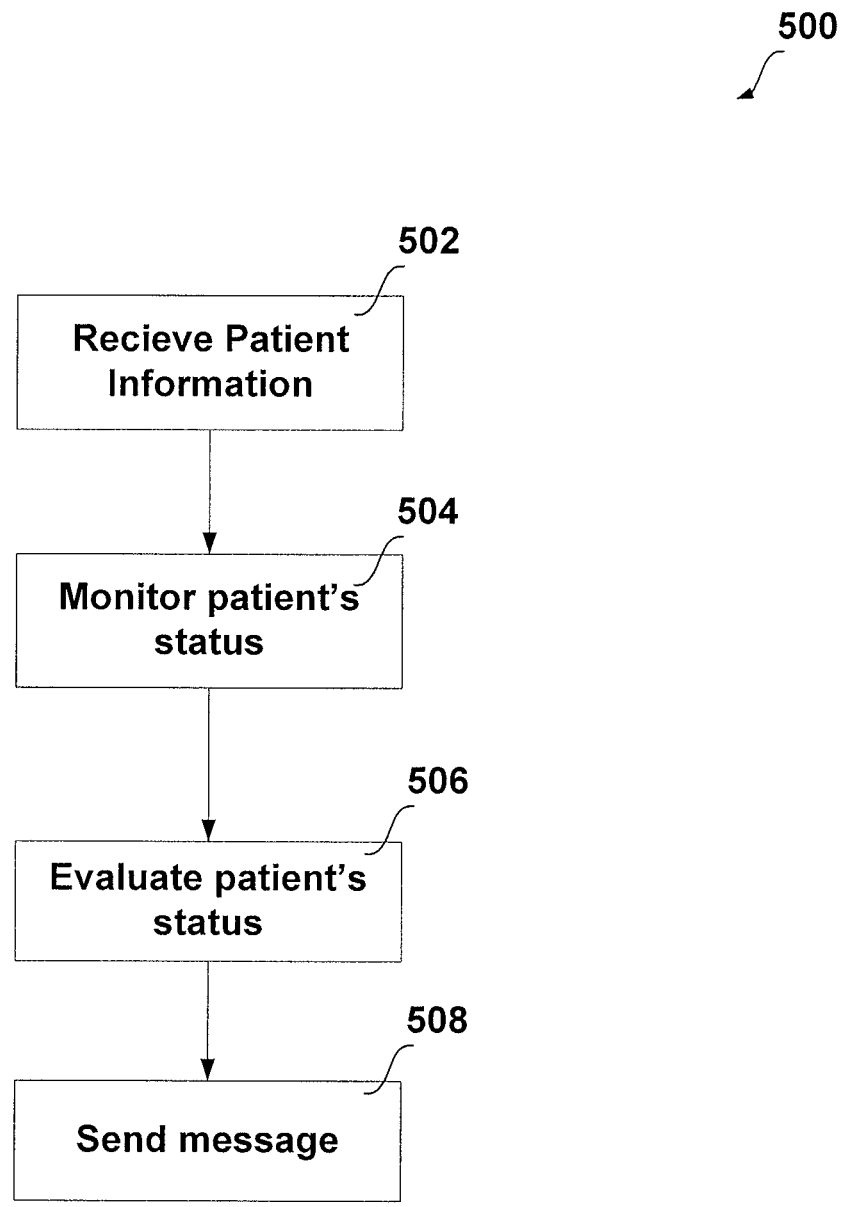
FIG. 5 is a flow chart of operations of a rules manger software in a monitoring system for an NI-ICU.

FIG. 5 is a flow chart 500 of exemplary operations of the rules manager software 144. The instructions of the rules manager software 144 can be executed by a single computing device or by distributed multiple devices. The rules manager software 144 and modules associated with the software may be standalone programs. The rules manager software 144 receives (502) patient medical information collected from a wide variety of clinical devices. The rules manager software 144 monitors (504) the patient's current clinical data in real-time and checks the validity of certain rule or a set of rules defined for a specific patient in the virtual ICU of the NI-ICU system. The monitoring and checking may include searching, accessing and retrieving patient records stored in the centralized server 102 and data depository 104 for data comparison and updating. By continuously evaluating (506) patient information, the rules manager software 144 can detect abnormal symptoms or risk factors in the conditions of the patients in a timely fashion. In the event of a violation of a rule, The rules manager software 144 can send (508) a message, e.g., including an alert, to the centralized console 112, such that the medical team 160 can take proper actions.

In some implementation, the location of the patient can be reported to relevant medical personnel and departments for appropriate medical care arrangement and scheduling. The rules manager software 144 may also be configured to recommend possible treatment procedures, e.g., at critical times, such that both the local medical team 158 in the virtual ICUs and the medical team 160 in the ICU 110 can work together. The physicians at different locations may collaborate on diagnosis and treatment plans through the communicator 140.

The apparatus, methods, flow diagrams, and structure block diagrams described in this patent document can be implemented in computer processing systems including program code comprising program instructions that are executable by the computer processing system.

Figure 6:
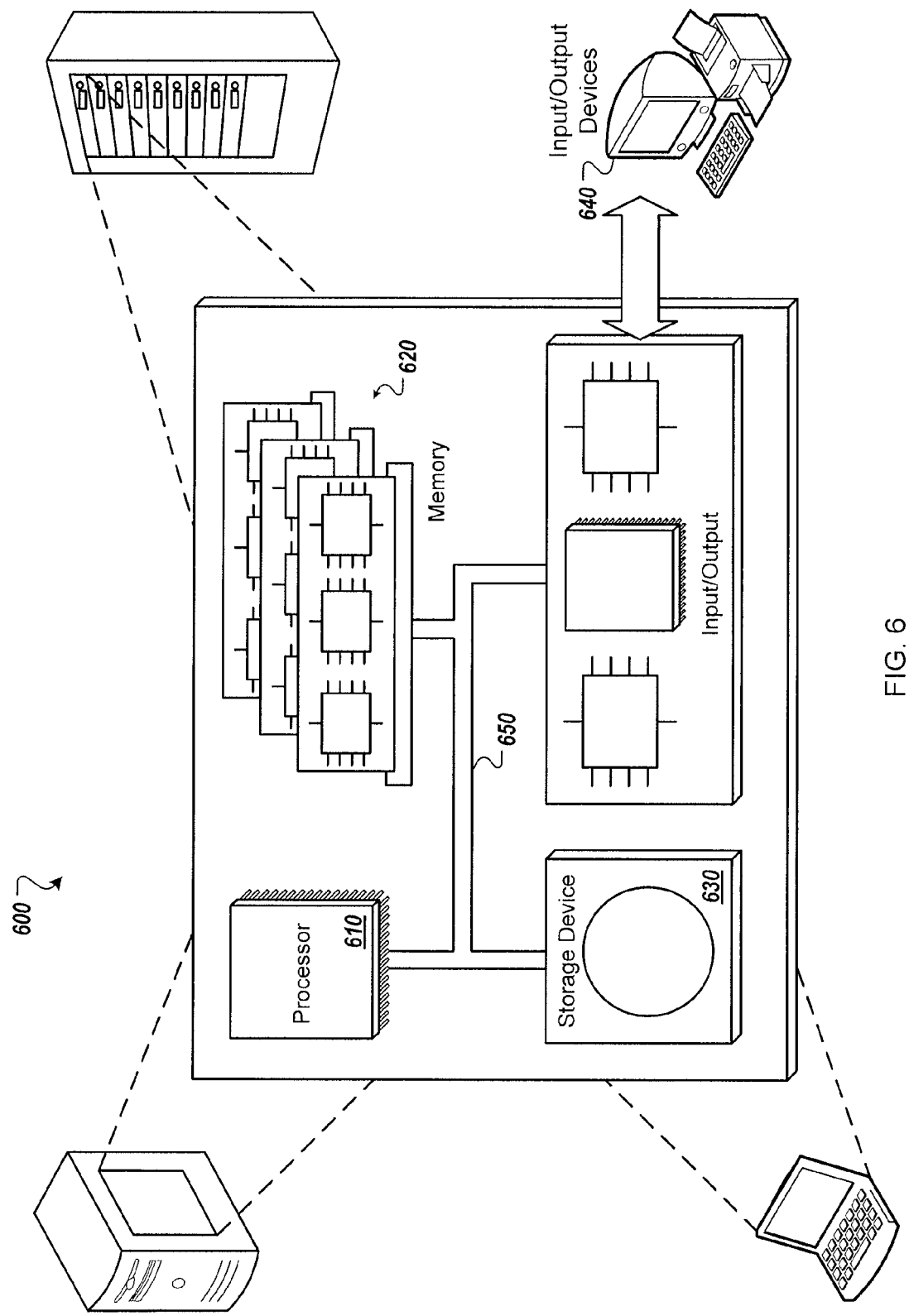
FIG. 6 shows a schematic diagram of an example computer system.

FIG. 6 is a schematic diagram of an example computer system 600. The system 600 can be used for practicing operations described above. The system 600 can include a processor 610, a memory 620, a storage device 630, and input/output devices 640. Each of the components 610, 620, 630, and 640 are interconnected using a system bus 650. The processor 610 is capable of processing instructions within the system 600. These instructions can implement one or more aspects of the systems, components and techniques described above. In some implementations, the processor 610 is a single-threaded processor. In other implementations, the processor 610 is a multi-threaded processor. The processor 610 can include multiple processing cores and is capable of processing instructions stored in the memory 620 or on the storage device 630 to display graphical information for a user interface on the input/output device 640.

The memory 620 is a computer readable medium such as volatile or non volatile that stores information within the system 600. The memory 620 can store processes related to various functionality, for example. The storage device 830 is capable of providing persistent storage for the system 600. The storage device 630 can include a floppy disk device, a hard disk device, an optical disk device, or a tape device, or other suitable persistent storage mediums. The storage device 630 can store the various databases described above. The input/output device 640 provides input/output operations for the system 600. The input/output device 640 can include a keyboard, a pointing device, and a display unit for displaying graphical user interfaces.

The computer system 600 illustrates one example of a computing device. In general, embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art can effect alterations, modifications and variations to the examples without departing from the scope of the invention.

What is claimed:

1. A computer implemented method for monitoring patients comprising:
   during a period of time, continuously monitoring patients released from an intensive care unit in a healthcare environment,
   wherein the at least some of the released patients who are being continuously monitored are at a recovery stage between a first recovery stage of patients remaining at the intensive care unit and a second recovery stage of patients only needing periodic routine examination without continuous monitoring;
   receiving medical information of a patient released from the intensive care unit and being continuously monitored;
   evaluating conditions of the released patient on a computing device by applying one or more formula-generated patient specific rules to the medical information of the released patient; and
   sending a message to a health care professional based on the evaluated conditions of the released patient, wherein the message prompts the health care professional to determine
      whether to readmit the released patient to the intensive care unit in response to the evaluated conditions indicating the patient is in the first recovery stage or
      whether to discontinue continuously monitoring the released patient in response to the evaluated conditions indicating the patient is in the second recovery stage that needs periodic routine examination without continuous monitoring.

2. The method of claim 1 further comprising monitoring the released patient using a clinical medical device.

3. The method of claim 1 further comprising determining a location of the released patient using an electronic device.

4. The method of claim 3 wherein the electronic device is integrated with a device collecting the medical information of the released patient at the location.

5. The method of claim 3 wherein the electronic device comprises a portable electronic device.

6. The method of claim 1 further comprising:
   storing the medical information of the released patient in a centralized data repository; and
   providing users at the intensive care unit with access to the centralized data repository.

7. The method of claim 6 further comprising authenticating a user when the user requests to access the centralized data repository.

8. The method of claim 6 further comprising:
   updating the medical information of the released patient in the centralized data repository; and
   updating the one or more rules in connection with the medical information.

9. The method of claim 1 comprising providing computer-generated treatment recommendations to at least one of a location of the released patient and the intensive care unit.

10. The method of claim 1 comprising displaying the conditions of the released patient in the intensive care unit continuously.

11. A computer-readable storage medium for storing instructions that are executable by a computer, the execution of the instructions causes the computer to:
   for a period of time, continuously monitor patients released from an intensive care unit in a healthcare environment;
   wherein at least some of the released patients who are being continuously monitored are at a recovery stage between a first recovery stage of patients remaining at the intensive care unit and a second recovery stage of patients only needing periodic routine examination without continuous monitoring;
   receive medical information of a patient released from the intensive care unit and being continuously monitored;

evaluate conditions of the released patient by applying one or more formula-generated patient specific rules to the patient information of the released patient; and send a message to a health care professional based on the evaluated conditions of the released patient, wherein the message prompts the health care professional to determine whether to readmit the released patient to the intensive care unit in response to the evaluated conditions indicating the patient is in the first recovery stage or whether to discontinue continuously monitoring the released patient in response to the evaluated conditions indicating the patient is in the second recovery stage that needs periodic routine examination without continuous monitoring.

12. The computer-readable storage medium of claim 11 further comprising causing the computer to monitor the released patient using a clinical medical device.

13. The computer-readable storage medium of claim 11 further comprising causing the computer to determine a location of the released patient using an electronic device.

14. The computer-readable storage medium of claim 13 wherein the electronic device is integrated with a device collecting the medical information of the released patient at the location.

15. The computer-readable storage medium of claim 13 wherein the electronic device comprises a portable electronic device.

16. The computer-readable storage medium of claim 11 further comprising causing the computer to:
store the medical information of the released patient in a centralized data repository; and
provide users at the intensive care unit with access to the centralized data repository.

17. The computer-readable storage medium of claim 16 further comprising causing the computer to authenticate a user when the user requests to access the centralized data repository.

18. The computer-readable storage medium of claim 16 further comprising causing the computer to:
update the medical information of the released patient in the centralized data repository; and
update the one or more rules in connection with the medical information.

19. The computer-readable storage medium of claim 11 comprising providing computer-generated treatment recommendations to at least one of a location of the released patient and the intensive care unit.

20. The computer-readable storage medium of claim 11 comprising displaying the conditions of the released patient in the intensive care unit continuously.

21. A system comprising:
a computing device comprising
a memory; and
an engine configured to
continuously monitor patients released from an intensive care unit in a healthcare environment for a period of time, wherein at least some of the released patients who are being continuously monitored are at a recovery stage between a first recovery stage of patients remaining at the intensive care unit and a second recovery stage of patients only needing periodic routine examination without continuous monitoring;

receive medical information of a patient released from the intensive care unit and being continuously monitored, evaluate conditions of the released patient by applying one or more formula-generated patient specific rules to the medical information of the released patient, and send a message to a health care professional based on the evaluated conditions of the released patient, wherein the message prompts the health care professional to determine whether to readmit the released patient to the intensive care unit in response to the evaluated conditions indicating the patient is in the first recovery stage or whether to discontinue continuously monitoring the released patient in response to the evaluated conditions indicating the patient is in the second recovery stage that needs periodic routine examination without continuous monitoring.

22. The system of claim 21 wherein the medical information is obtained by monitoring the released patient using a clinical medical device.

23. The system of claim 21 wherein the medical information comprises information about a location of the released patient determined by an electronic device.

24. The system of claim 23 wherein the electronic device is integrated with a device collecting the medical information of the released patient at the location.

25. The system of claim 23 wherein the electronic device comprises a portable electronic device.

26. The system of claim 21 wherein the memory comprises a centralized data repository for storing the medical information of the released patient and the computer provides users at the intensive care unit with access to the centralized data repository.

27. The system of claim 26 wherein the computer authenticates a user when the user requests to access the centralized data repository.

28. The system of claim 26 wherein the engine is configured to update the medical information of the released patient in the centralized data repository and the one or more rules in connection with the medical information.

29. The system of claim 21 wherein the engine is configured to provide computer-generated treatment recommendations to at least one of a location of the released patient and the intensive care unit.

30. The system of claim 21 wherein the engine is configured to display the conditions of the released patient in the intensive care unit continuously.

* * * * *